(12) United States Patent
Dowdall et al.

(10) Patent No.: US 10,768,027 B2
(45) Date of Patent: Sep. 8, 2020

(54) METHOD AND SYSTEM FOR MONITORING BUILDING STRUCTURES

(71) Applicant: Structural Health Systems, Inc., Cambridge, MA (US)

(72) Inventors: Brendan P. Dowdall, Bedford, MA (US); Ryan P. Twomey, Dedham, MA (US); Frank Arcoleo, Somerville, MA (US); Mark D. Halfman, Newtonville, MA (US); James Paris, Boston, MA (US)

(73) Assignee: Hilti AG, Schaan (LI)

(*) Notice: Subject to any disclaimer, the term of this patent is extended or adjusted under 35 U.S.C. 154(b) by 0 days.

(21) Appl. No.: 16/459,151

(22) Filed: Jul. 1, 2019

(65) Prior Publication Data

US 2019/0323865 A1    Oct. 24, 2019

Related U.S. Application Data

(62) Division of application No. 15/371,880, filed on Dec. 7, 2016, now Pat. No. 10,386,210.

(60) Provisional application No. 62/371,559, filed on Aug. 5, 2016, provisional application No. 62/263,961, filed on Dec. 7, 2015.

(51) Int. Cl.
| | |
|---|---|
| *G01K 1/00* | (2006.01) |
| *G01K 13/00* | (2006.01) |
| *G01K 7/00* | (2006.01) |
| *G01D 11/00* | (2006.01) |
| *G01N 33/38* | (2006.01) |
| *E04B 1/16* | (2006.01) |
| *G01J 1/42* | (2006.01) |
| *G08C 17/02* | (2006.01) |

(52) U.S. Cl.
CPC ............ *G01D 11/00* (2013.01); *E04B 1/16* (2013.01); *G01J 1/4204* (2013.01); *G01N 33/383* (2013.01); *G08C 17/02* (2013.01)

(58) Field of Classification Search
USPC .................. 374/142, 100, 163, 166, 141
See application file for complete search history.

(56) References Cited

U.S. PATENT DOCUMENTS

| | | |
|---|---|---|
| 4,480,929 A | 11/1984 | Hansen |
| 4,943,930 A | 7/1990 | Radjy |
| 5,041,987 A | 8/1991 | Kuwahara et al. |
| 7,551,058 B1 | 6/2009 | Johnson et al. |

(Continued)

FOREIGN PATENT DOCUMENTS

| | | |
|---|---|---|
| CN | 205537774 U | 8/2016 |
| CN | 205538970 U | 8/2016 |

(Continued)

OTHER PUBLICATIONS

Command Center, accessed on Dec. 14, 2016, http://www.maturitycentral.com/.

(Continued)

*Primary Examiner* — Mirellys Jagan
(74) *Attorney, Agent, or Firm* — Foley Hoag LLP; Rajesh Vallabh

(57) ABSTRACT

Methods and systems are disclosed for monitoring properties of building structures (e.g., monitoring the strength and humidity of concrete structures) using sensor devices embedded in the building structures. The sensor devices collect sensor data and wirelessly transmit the data to portable computer devices operated by users.

7 Claims, 25 Drawing Sheets

(56) References Cited

U.S. PATENT DOCUMENTS

| | | |
|---|---|---|
| 8,032,244 B2 | 10/2011 | Trost et al. |
| 8,423,300 B1 | 4/2013 | diGirolamo |
| 10,386,210 B2 | 8/2019 | Dowdall et al. |
| 2004/0004554 A1 | 1/2004 | Srinivasan et al. |
| 2007/0046479 A1 | 3/2007 | Hines |
| 2007/0116402 A1 | 5/2007 | Slade et al. |
| 2007/0126433 A1 | 6/2007 | Theophanous et al. |
| 2011/0142091 A1 | 6/2011 | Wardle et al. |
| 2012/0173150 A1 | 7/2012 | Romero et al. |
| 2013/0271011 A1 | 10/2013 | Williams et al. |
| 2014/0210494 A1 | 7/2014 | Ghods et al. |
| 2015/0048844 A1 | 2/2015 | Neikirk et al. |

FOREIGN PATENT DOCUMENTS

| | | |
|---|---|---|
| WO | WO-2012024393 A1 | 2/2012 |
| WO | WO-2013188867 A1 | 12/2013 |
| WO | WO-2015172231 A1 | 11/2015 |

OTHER PUBLICATIONS

ConReg, accessed on Dec. 14, 2016, http://www.controls-group.com/eng/concrete-testing-equipment/.
Giatec Scientific, accessed on Dec. 15, 2016, http://www.giatecscientific.com/.
Hard Track, accessed on Dec. 15, 2016, http://www.wakeinc.com/.
Heat Watch by Germann, accessed on Dec. 15, 2016, http://germann.org/products-by-application/temperature-measurement/heatwatch.
IntelliRock, accessed on Dec. 15, 2016, http://www.flir.com/instruments/concrete/display/?id=44885.
International Search Report and Written Opinion for PCT/US2016/065335, dated Mar. 24, 2017.
Kraft Curing, accessed on Dec. 15, 2016, http://www.kraft-systems.com/index.php/en/equipment/wireless-system.
Pilieci, Vito, accessed on Dec. 15, 2016, http://ottawacitizen.com/business/local-business/buried-sensors-cement-giatecs-reputation-for-concrete-solutions.

< Mark's Test Project 1                                      Edit

DETAILS

| | |
|---:|:---|
| Name | 1 |
| Address | Boston, MA |
| Mix Design | Generic: 4000 ACI Compliant |
| Last Update | 12/05/2016 at 2:19 PM |

Email Graphs

DRYING STATISTICS

| | |
|---:|:---|
| Current Max | 86% RH |
| Current Min | 86% RH |

1 SENSOR

✓ 05dfe8 📶 (RSSI: -94)                                      >
Last connected: 12/05/2016 at 2:19 PM

Add Sensor

📁                    ⚙
Projects              Settings

FIG. 1E

METHOD AND SYSTEM FOR MONITORING BUILDING STRUCTURES

CROSS REFERENCE TO RELATED APPLICATIONS

This application claims priority from U.S. patent application Ser. No. 15/371,880 filed on Dec. 7, 2016 entitled METHOD AND SYSTEM FOR MONITORING BUILDING STRUCTURES, which claims the benefit of U.S. Provisional Patent Application No. 62/263,961 filed on Dec. 7, 2015 entitled METHOD AND SYSTEM FOR MONITORING THE STRENGTH AND HUMIDITY OF CONCRETE STRUCTURES and U.S. Provisional Patent Application No. 62/371,559 filed on Aug. 5, 2016 entitled METHOD AND SYSTEM FOR MONITORING BUILDING STRUCTURES, all of which applications are hereby incorporated by reference.

BACKGROUND

The present application relates generally to methods and systems for monitoring properties of building structures, e.g., monitoring the strength and humidity of concrete slabs and other concrete structures.

BRIEF SUMMARY OF THE DISCLOSURE

In accordance with one or more embodiments, a sensor device is disclosed for monitoring properties of a building material within which the sensor device can be embedded. The sensor device is packaged in a removable light blocking packaging. The sensor device includes a controller, memory associated with the controller, one or more sensors connected to the controller for measuring one or more properties of the building material, an optical sensor connected to the controller for detecting the presence of light, a power supply for powering components of the sensor device, and a communication module connected to the controller. The controller is configured to receive a signal from the optical sensor when light is detected after the sensor device is removed from the light blocking packaging, and to responsively activate the sensor device. The controller is also configured to receive data on the one or more properties of the building material from the one or more sensors after the sensor device is removed from the light blocking packaging and embedded in the building material, and to wirelessly transmit data on the one or more properties of the building material to an electronic device external to the building material through the communication module.

In accordance with one or more further embodiments, a portable computer device is disclosed. The computer device includes at least one processor, memory associated with the at least one processor, a display, a communication module connected to the at least one processor for receiving data wirelessly from remote devices, and a program supported in the memory for monitoring properties of a building structure. The program having a plurality of instructions stored therein which, when executed by the at least one processor, cause the at least one processor to: (a) receive data via the communication module from a plurality of sensor devices embedded in the building structure, (b) calculate a plurality of metrics relating to the building structure based on the data received in (a), (c) record locations on a floorplan where each of the plurality of sensor devices is positioned, and (d) synchronize information relating to said sensor devices or the building structure with portable computer devices operated by other users. In one or more embodiments, the metrics include building structure strength, seismic events, vibration effects, material pH levels, gas and particle presence, structure load, crack detection, mold formation, and moisture presence.

In accordance with one or more further embodiments, a sensor device is disclosed for monitoring properties of a building material within which the sensor device can be embedded. The sensor device includes a housing, a controller in the housing, memory in the housing associated with the controller, a power supply in the housing for powering components of the sensor device, a communication module in the housing connected to the controller, and one or more sensors for measuring one or more properties of the building material. The one or more sensors are outside the housing and connected to the controller by an electrical cable. The controller is configured to receive data on the one or more properties of the building material from the one or more sensors and to wirelessly transmit data on the one or more properties of the building material to an electronic device external to the building material through the communication module.

BRIEF DESCRIPTION OF THE DRAWINGS

FIGS. 1D and 1E are screenshots illustrating sensor device information displayed to a user in accordance with one or more embodiments.

Like or identical reference numbers are used to identify common or similar elements.

DETAILED DESCRIPTION

Various embodiments disclosed herein are directed to methods and systems for monitoring one or more properties of building materials, including but not limited to concrete, asphalt, and epoxy. In some embodiments, the methods and systems are used for monitoring one or more properties of an ambient environment (e.g., gas ambient such as air, liquid ambient). In some embodiments, properties being monitored include, but are not limited to, the strength and/or relative humidity (RH) of a building structure such as a concrete structure. The properties are monitored using one or more sensor devices embedded in the structure, which collect and send sensor data wirelessly to smartphones or other computer devices operated by users outside the building structure. Various other building material properties may also be sensed including, but not limited to, temperature, vibration, pH, gas and particle presence, load, and acoustic properties.

In accordance with one or more embodiments, the sensor system generally includes two components: a smartphone (or other computer) app and a hardware sensor device. The smartphone app connects to the sensor device using the Bluetooth or Bluetooth Low Energy (BLE) protocol or other wireless communications protocols such as, e.g., ANT, IEEE 802.11 and WiFi, RFID, NFC, Thread, LoRa, and ZigBee. The sensor device is a combination sensing device and datalogger, with a battery that lasts for a given period of time, which can vary based on intended use. By way of example, in some jobs, the battery should last for 28 days, and in other jobs it should last for two years or more.

Figure 1A:
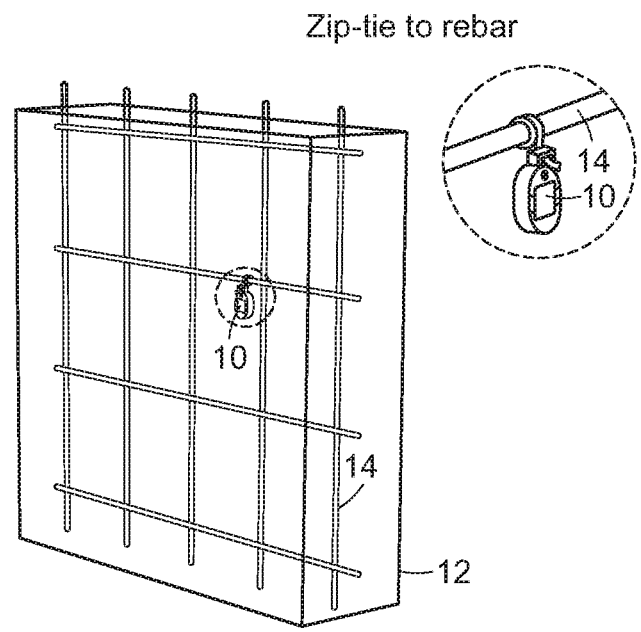
FIG. 1A illustrates an exemplary concrete sensor device embedded in a concrete structure for monitoring the strength and humidity of the structure in accordance with one or more embodiments.

FIG. 1A illustrates an exemplary concrete sensor device 10 embedded in a concrete structure 12 for monitoring the strength and humidity of the structure. The concrete sensor device 10 is attached to rebar 14 in the structure using a cable tie 16 (also referred to as a zip tie) or other attachment mechanism. In addition to rebar 14, the sensor device 10 can also be attached to other structures within the building material including, but not limited to metal mesh, pipes, or conduits.

Figure 1B:
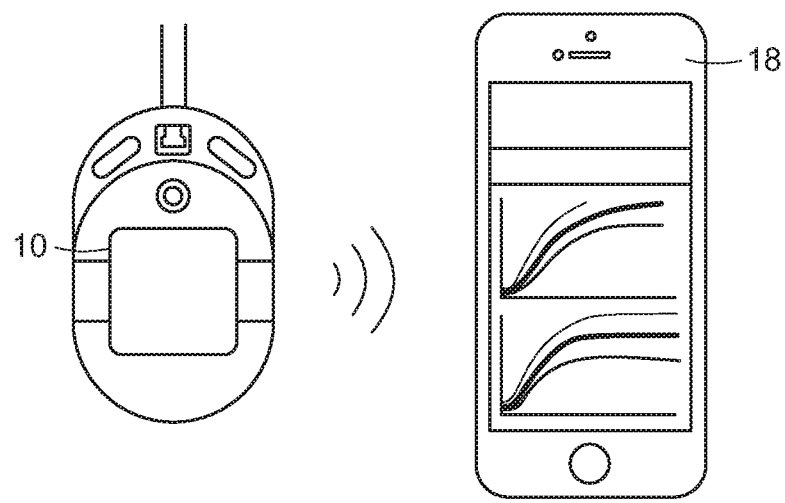
FIG. 1B illustrates wireless communication between the sensor device in accordance with one or more embodiments and a smartphone.

FIG. 1B illustrates wireless communication between the sensor device 10 and a smartphone 18.

In accordance with one or more embodiments, the smartphone app uses the smartphone's camera to allow the user to scan a code shown on the sensor device 10, e.g., a QR code. Accordingly, no extra hardware such as a reader is needed to use the system. Once scanned, the app searches for a sensor device 10 broadcasting a matching identifier. When found, the app will then periodically poll the sensor device 10 for updated data.

Figure 1C:
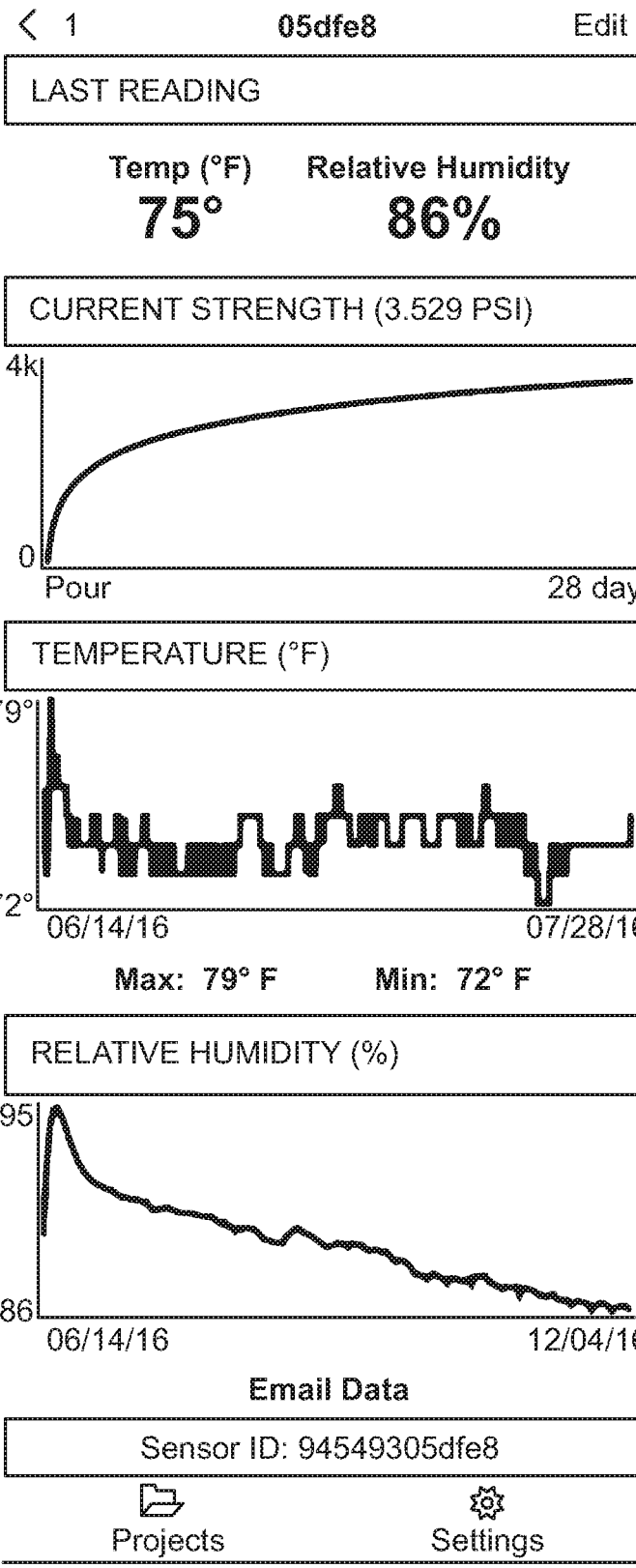
FIG. 1C is a screenshot illustrating exemplary strength calculations and temperature and humidity data displayed to a user in accordance with one or more embodiments.

The smartphone app calculates various metrics based on sensor data, including the strength of concrete (using, e.g., the methods described in ASTM C-1074). The app interprets the data received from sensor devices using actual mix designs while additionally providing a log of raw data content to users. The system utilizes a library of data on concrete mix designs in lieu of general predictions or users needing to test concrete themselves. FIG. 1C is an exemplary screenshot illustrating strength calculations and temperature and humidity data displayed to a user on the smartphone in graphs. In accordance with one or more embodiments, users can share or view the graphs and displayed metrics with other devices.

In accordance with one or more embodiments, the smartphone app transmits data received from the sensor devices to a remote computer system in the cloud, which generates graphs based on the data, and transmits the graphs to the smartphone to be displayed on the smartphone or shared with other devices.

The app can also save floor plan information, e.g., with a "pin drop" feature that allows users to set where on a floor plan a sensor device 10 is placed.

The app can also synchronize sensor data, floor plan data, and other data with other team members.

Figure 1D:
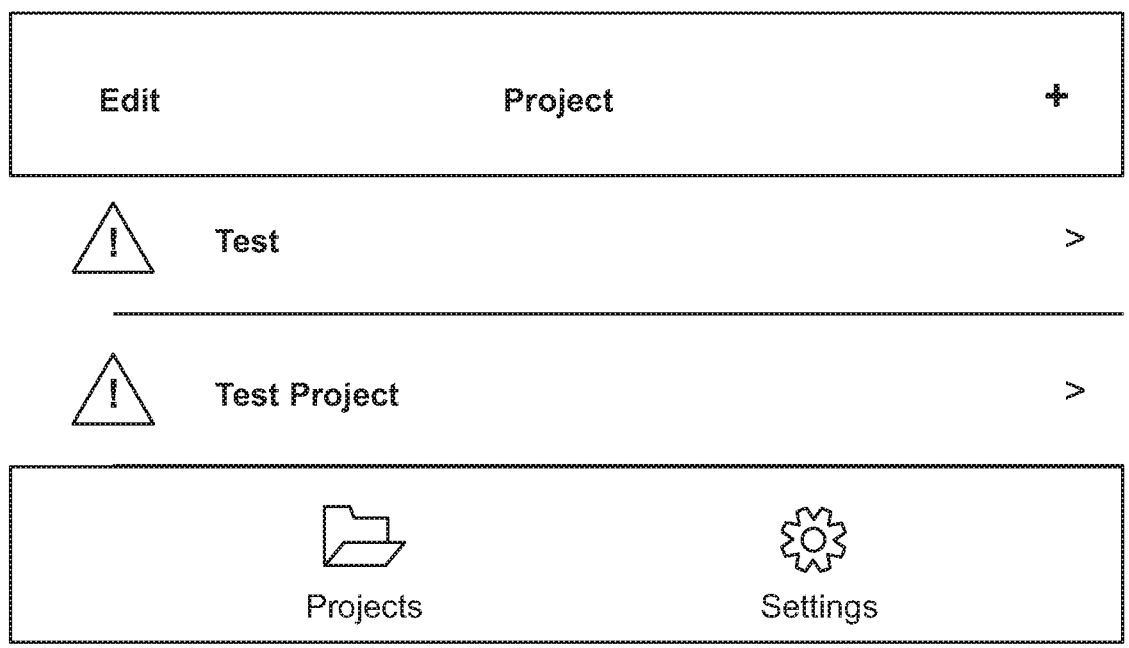

Sensor devices are categorized by project and subcategorized by floor. Projects can be described by a project name and project address. Floors are described by a floor name, concrete mix design and summary statistics of the sensor devices on that floor. FIGS. 1D and 1E are exemplary screenshots displayed on a user's smartphone 18 illustrating such sensor information.

Figure 2:
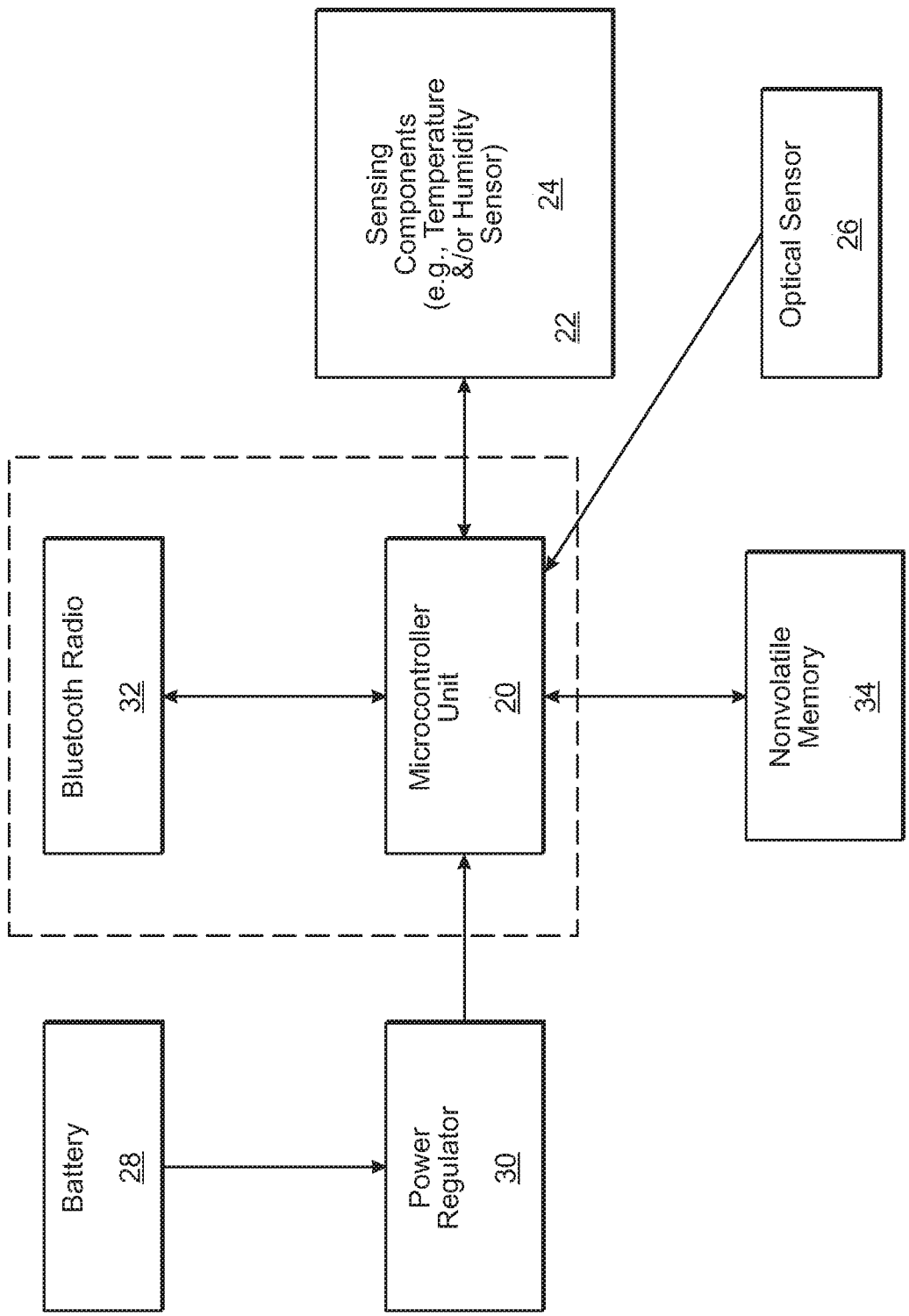
FIG. 2 is a schematic block diagram illustrating select components of a concrete sensor device in accordance with one or more embodiments.

FIG. 2 is a schematic block diagram illustrating select components of a concrete sensor device 10 in accordance with one or more embodiments. The sensor device 10 includes a printed circuit board (PCB) assembly with an attached battery. The PCB assembly includes a microcontroller unit 20, which receives temperature and humidity data from a temperature sensor 22 and a humidity sensor 24.

The microcontroller unit 20 also receives data from an optical sensor 26. The device is powered by the battery 28 through a power regulator 30. The device communicates with the smartphone app through a radio 32. Data is stored in a non-volatile memory 34.

In accordance with one or more embodiments, the sensor device 10 is stored in a light-blocking packaging that is removed by the installer prior to installation. When the sensor device 10 is inside a package, it retrieves an optical sensor reading every few seconds. If two consecutive readings indicate the sensor 26 is in light, it transitions to the "waiting for pour" state. In this manner, the sensor activation is not dependent on the installer providing an activation signal (e.g., flipping a mechanical switch, providing a wireless signal via an app, etc.), and hence eliminates potential user error caused by a user forgetting to activate the sensor device 10 upon installation.

Various other sensor device activation techniques are also possible. For example, the sensor device may include a removable streamer or tag that, when removed by the installer, activates the sensor device. Also, the sensor device may include a thin filament in the zip-tie hole that is broken when a zip-tie is inserted in the hole. Breakage of the filament is detected and responsively actives the sensor device. As another example, the sensor device may include a pH sensor, which can determine a highly alkaline environment, indicating presence of concrete, and in response active the sensor device. As yet another example, the sensor device may include an NFC reader, allowing a smartphone to turn on the sensor device. In this case, the smartphone broadcasts an NFC signal, and the NFC reader on the sensor device listens for it to activate the device.

Figure 3A:
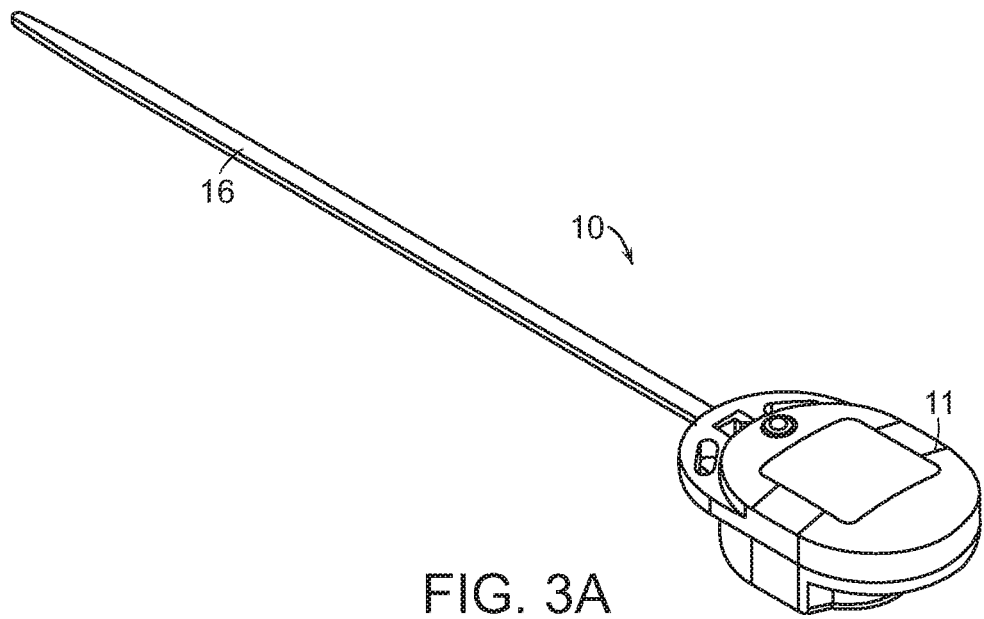
FIGS. 3A-3C illustrate an exemplary sensor device including an overmolded body in accordance with one or more embodiments.
Figure 3B:
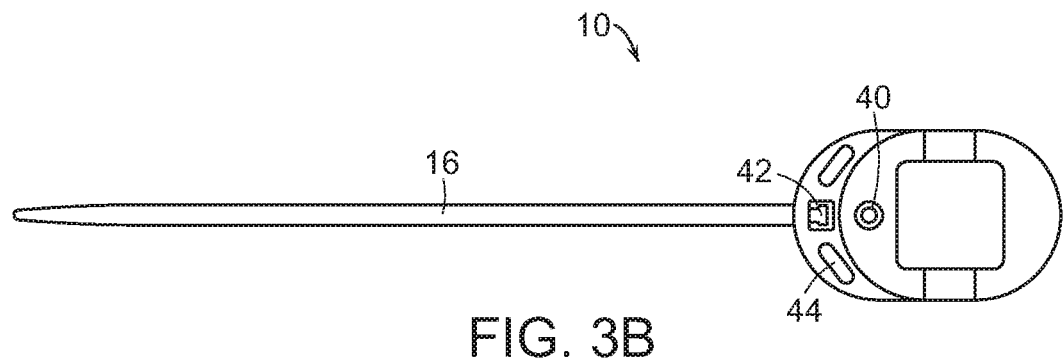
Figure 3C:
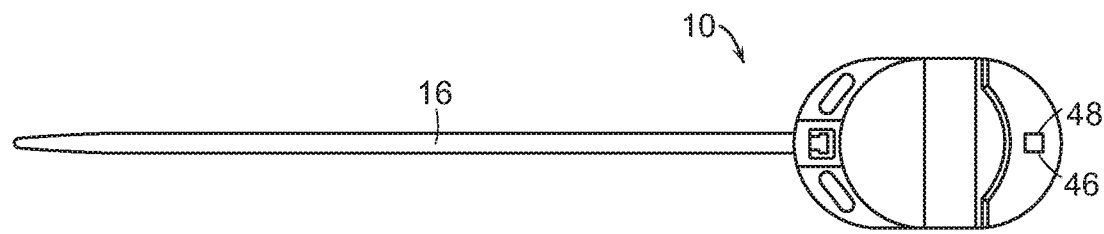

FIGS. 3A-3C are illustrations of an exemplary sensor device 10 including an overmolded body 11, according to some embodiments. FIG. 3A is a perspective view of the sensor device 10 including the overmolded body, FIG. 3B is a front view of the sensor device 10 including the overmolded body, and FIG. 3C is a back view of the sensor device 10 including the overmolded body. The overmolded body is formed around a PCB that comprises the components forming the sensor device 10. The overmolded body may be formed of plastic and/or rubber.

As shown in FIG. 3B, the front side of the sensor device 10 includes a light guide 40 located over the optical sensor 26 within the body so as to enable light to pass through to the optical sensor 26 on the PCB. The sensor device 10 can also include a clear or semi-clear portion (e.g., a transparent plastic faceplate) that allows light to pass through to the optical sensor 26.

A cable tie 16 and cable tie opening 42 is provided so as to enable easy attachment of the sensor device 10 to construction structures, such as rebar 14 within concrete slabs. Additionally, or alternatively, one or more attachment openings 44 enable the attachment of the sensor device 10 to construction structures using any suitable attachment methods, such as metal wires, cable ties, and/or the like.

As shown in FIG. 3C, the back side of the sensor device body (which may, e.g., be a plastic body) includes a sensor opening 46, which enables sensing components inside the device to sense one or more properties of the building materials (e.g., temperature and/or humidity). In other embodiments the sensor opening may be provided on the front side of the sensor device 10. A membrane filter 48 may be disposed in registry with the sensor opening (e.g., within the sensor opening, under the sensor opening, over the sensor opening). The membrane filter 48 allows moist vapor (e.g., moist air) into the body (where it can be sensed via the relative humidity sensor mounted on the PCB), while inhibiting or preventing liquid water, chemicals, debris, etc. from entering. In some embodiments, the membrane is a polytetrafluoroethylene (PTFE) membrane, such as an extruded PTFE (ePTFE) membrane. In some embodiments, no membrane is used when the sensor being used requires physical contact the building material being sensed (e.g., a pH sensor).

Figure 4:
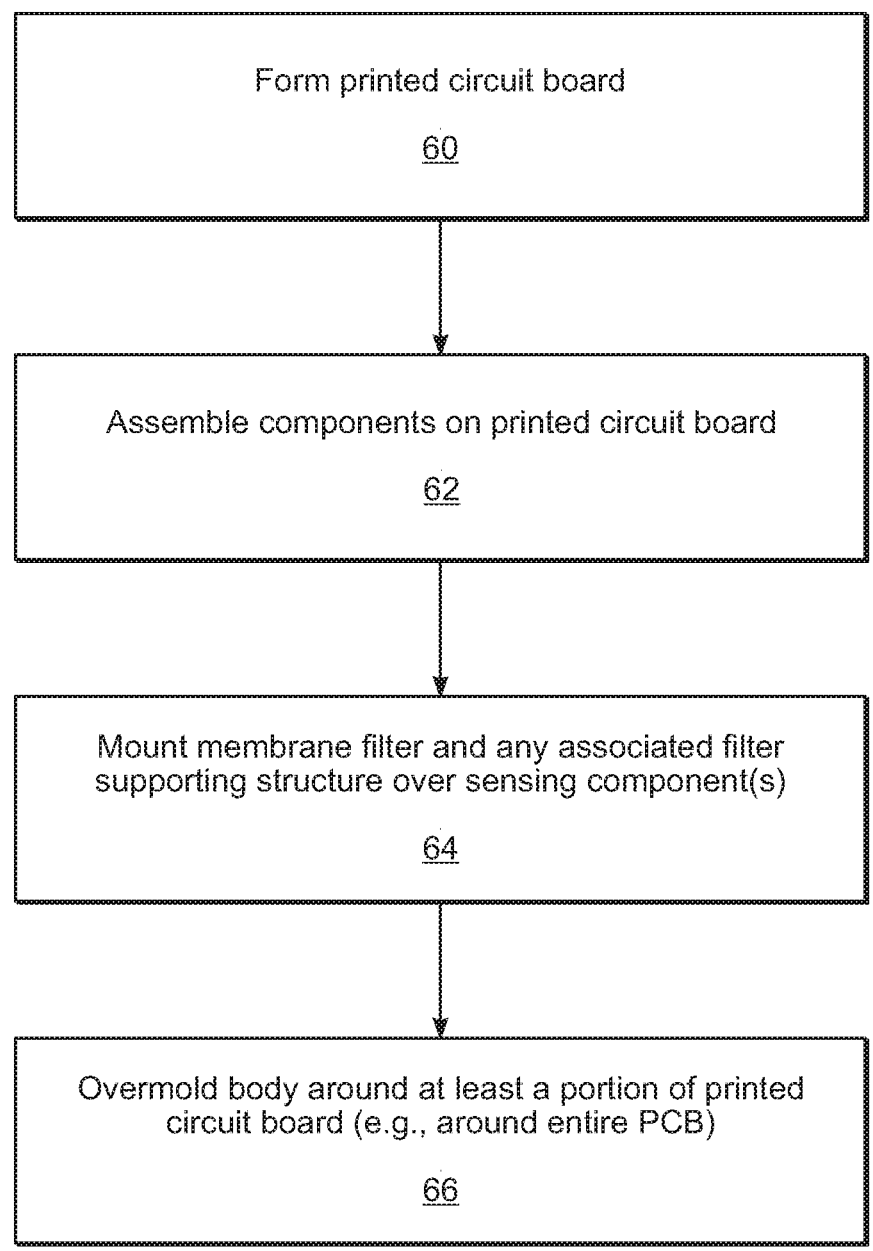
FIG. 4 is a flow chart illustrating an exemplary sensor device overmolding process in accordance with one or more embodiments.

FIG. 4 is a flow chart illustrating an exemplary sensor device overmolding method, according to some embodiments. The method includes, at step 60, forming a PCB, including forming electrical trace lines on a supporting board (e.g., metal lines, such as copper-based metal lines). The PCB may be a single layer and/or multi-layer board, and may include traces on a front side and/or a backside.

The method also includes assembling a plurality of components on the PCB at step 62. The components include one or more of the components shown in the schematic of FIG. 2, such as sensing components (e.g., temperature and/or humidity sensors 22, 24), optical sensor 26, microcontroller unit 20, radio, memory, power regulator, battery, resistors, capacitors, and/or inductors.

The method also includes mounting the membrane filter 48 over the sensing components at step 64. In some embodiments, an associated filter supporting structure is disposed over the membrane filter 48, such that the membrane filter 48 is disposed between the sensing components and the supporting structure. The filter supporting structure holds the membrane filter 48 securely in place over the sensing components.

The filter supporting structure may be a plastic structure formed via any suitable means, including, but not limited to, injection molding. The filter supporting structure includes an opening through which the membrane makes contact with the external environment (e.g., the building material), as shown in the perspective view of an exemplary filter supporting structure in FIG. 8.

In some embodiments, the filter supporting structure is secured to the PCB using, e.g., an epoxy or a silicone applied to one or more portions or all of the filter supporting structure in contact with the PCB.

The method further includes overmolding a body (e.g., a plastic and/or rubber body) around at least a portion or all of the PCB at step 66. The overmolding may be performed utilizing, e.g., a low pressure molding process. The overmolding process is performed so as to ensure that the opening of the filter supporting structure is not covered with molding material. The overmolded body for the sensor device 10 provides seamless encapsulation of the PCB and associated components of the sensor, which ensures that during use the building material in which the sensor is placed does not enter the sensor and damage the components or interfere with the operation of the sensor.

Figure 5:
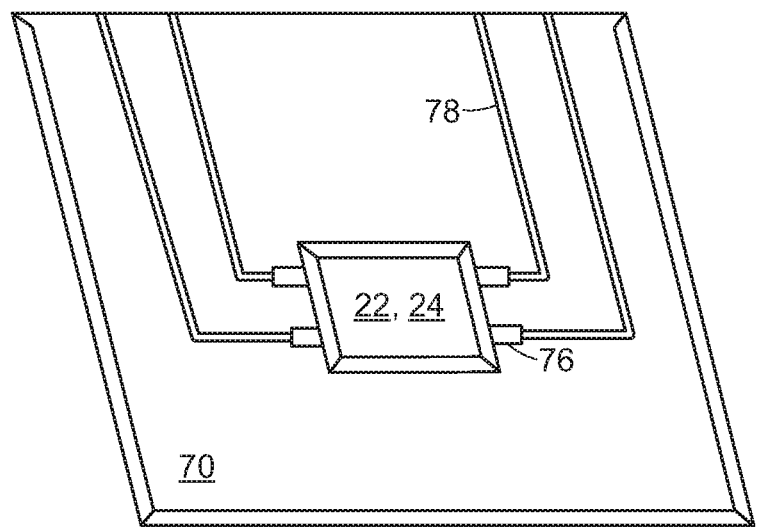
FIG. 5 is a perspective view of a portion schematically illustrating an exemplary printed circuit board (PCB) on which sensing components reside in accordance with one or more embodiments.

FIG. 5 is a perspective view of a portion of an exemplary PCB 70 on which the sensing component(s) (e.g., temperature and/or humidity sensing components 22, 24) reside, according to one embodiment. It should be appreciated that the other components may be placed on one or both sides of the PCB, which is not illustrated in FIG. 5. The sensing component(s) 22, 24 may be one or more packaged components including one or more semiconductor chips and including a plurality of metal leads 76 that upon mounting on the PCB enable electrical connections to metal traces on the PCB. The sensing component(s) 22, 24 backside may be placed in contact with a thermal pad on the PCB, which may be electrically connected to a ground plane of the PCB (e.g., a copper ground layer). The metal traces 78 electrically connected to the sensing component(s) may include a power line, a data line, a clock line, and a ground line.

Figure 6:
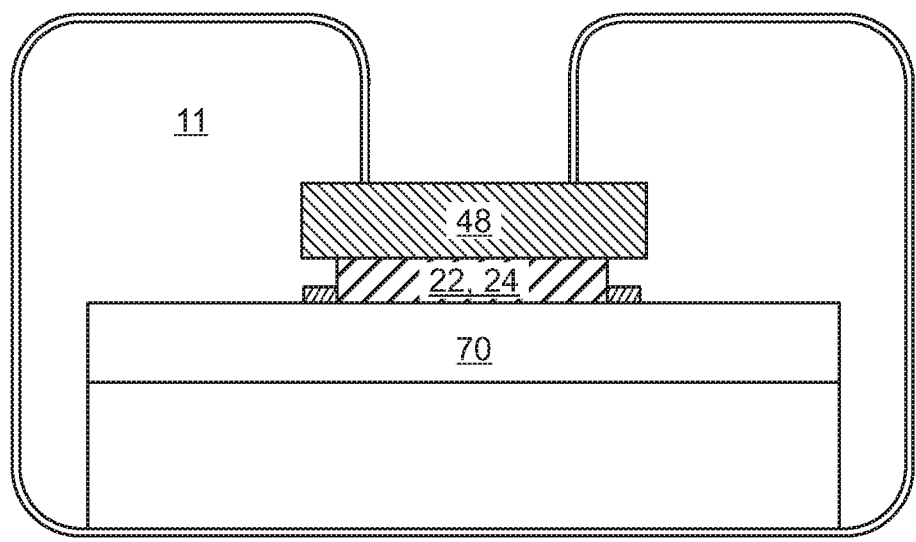
FIG. 6 is a cross-section view schematically illustrating an exemplary overmolded sensor device in accordance with one or more embodiments.

FIG. 6 is a cross-section view of an exemplary overmolded sensor device 10, according to some embodiments. As illustrated, in some embodiments, the membrane filter 48 is in contact with at least a portion of the sensing component(s). In some embodiments, at least a portion of the top face of the sensing component(s) is disposed in contact with the membrane filter 48. Such a configuration ensures that equilibrium with the external environment is attained quickly, which has been found to be especially important for relative humidity sensing. In contrast, the presence of a substantial gap between the sensing component and the membrane filter 48 may introduce an additional delay (e.g., more than one day) in attaining sensing equilibrium with the external environment.

In some embodiments, a gap of less than the thickness of the membrane is provided between the membrane backside and the top face of the sensing component. For example, the membrane filter 48 may have a thickness between about 0.75 mm and about 1.25 mm, and the gap thickness may be less than about 0.5 mm. In some embodiments, a gap of less than about half the thickness of the membrane filter 48 is provided between the membrane backside and the top face of the sensing component.

In some embodiments, the membrane filter 48 is held in contact with the sensing component(s) at least partially with a filter supporting structure. In other embodiments, the membrane filter 48 is held in contact with the sensing component without any associated supporting structure (as shown in the cross-section illustration of FIG. 6). To achieve such a configuration, the membrane filter 48 may be attached directly to the PCB and/or the sensing component(s), for example, utilizing an attachment material disposed around the perimeter of the membrane filter 48 and in contact with the PCB and/or sensing component(s).

Figure 7:
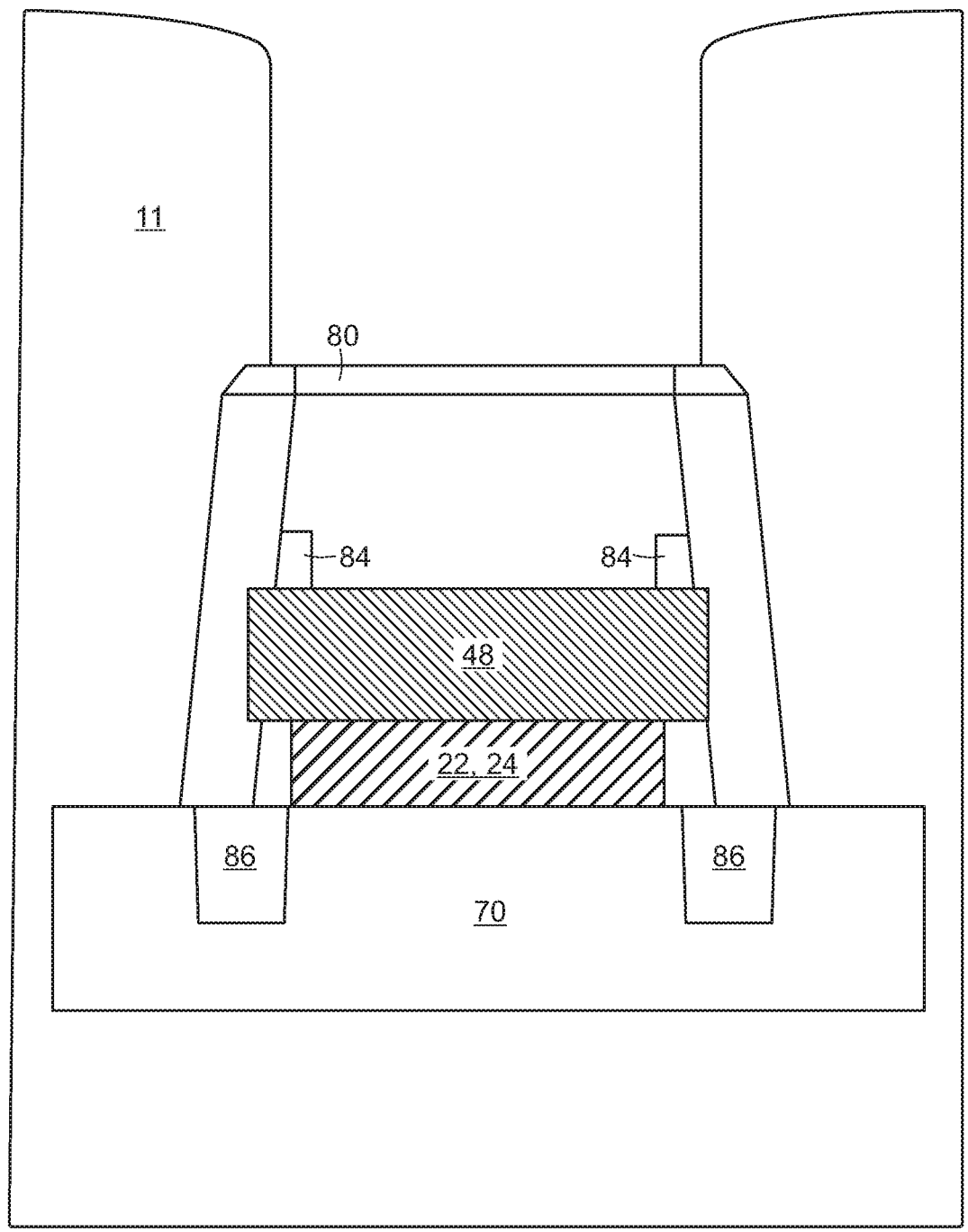
FIG. 7 is a cross-section view schematically illustrating an exemplary overmolded sensor device including a filter supporting structure in accordance with one or more embodiments.

FIG. 7 is a cross-section view schematically illustrating an exemplary sensor device including a filter supporting structure 80, according to some embodiments. The body of the sensor device may be an overmolded body 11 formed around a filter supporting structure 80 and leaving an opening to expose the membrane filter 48. Alternatively, the body may be formed from the attachment of injection molded housing portions that are adhered to each other and/or the filter supporting structure. Adherence may be achieved using epoxy, heat staking, ultrasonic welding, or other suitable adherence methods.

The filter supporting structure includes one or more shelf regions 84 that are in contact with the membrane filter 48 and hold the membrane filter 48 firmly in place over the sensing component(s) 22, 24. The filter supporting structure includes one or more legs 86 that are inserted into corresponding holes in the PCB and ensure proper place of the filter supporting structure over the sensing component(s). The filter supporting structure may be attached to the PCB using any suitable attachment material, for example, using an epoxy or a silicone. For example, an attachment material, such as epoxy or silicone may be disposed on the legs and/or base perimeter of the filter supporting structure. Such an assembly ensures that the membrane filter 48 is in a compressive state, and hence is firmly held in place.

Figure 8:
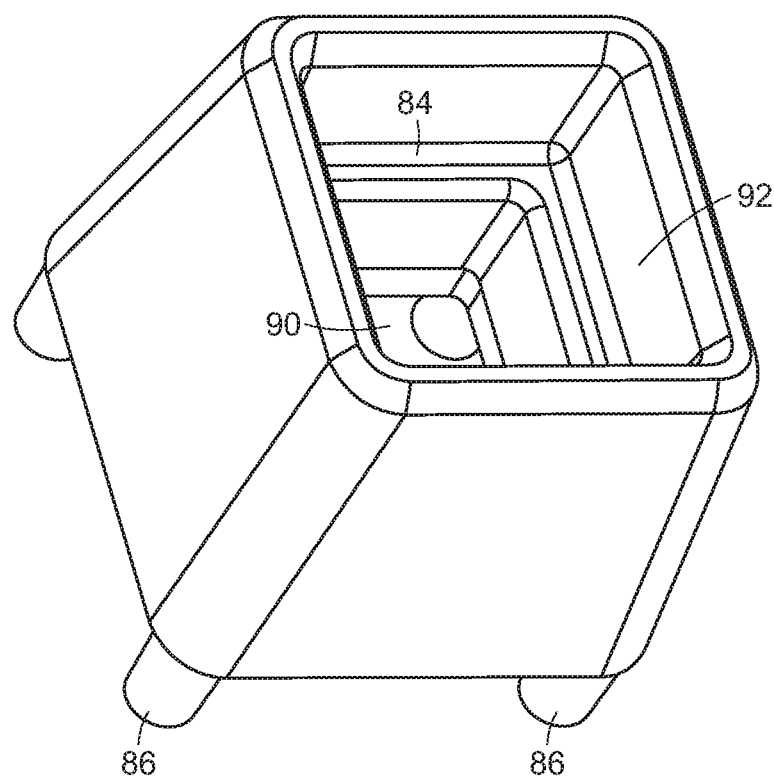
FIG. 8 is a perspective view of an exemplary filter supporting structure in a sensor device body in accordance with one or more embodiments.

FIG. 8 is a perspective view of an exemplary filter supporting structure, according to some embodiments. The filter supporting structure includes a shelf region around an opening 90, which holds the membrane filter 48 firmly in place. In some embodiments, the filter supporting structure includes a flange portion 92 over the shelf region(s). The flange configuration is useful for adhering the filter supporting structure to an injection molded housing, for instance, using epoxy, heat staking, ultrasonic welding, or other suitable adherence methods.

Figure 9:
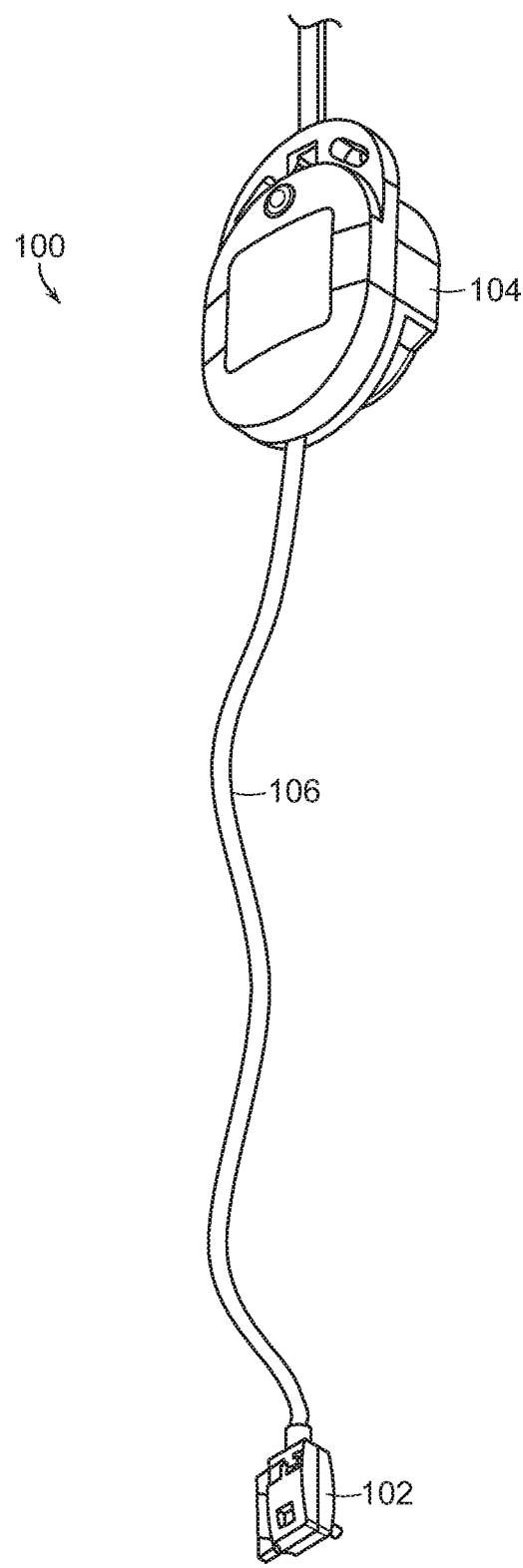
FIG. 9 is a perspective view of an exemplary sensor device having a sensing portion separated from a wireless communication portion in accordance with one or more embodiments.

FIG. 9 is a perspective view of an exemplary sensor device 100 having a separate sensing portion 102 electrically connected to a wireless communication portion 104, according to some embodiments. The sensing portion includes the sensing component(s) mounted on a PCB board, as described for FIGS. 5-7. The wireless communication portion includes at least one wireless communication component (e.g., radio component). In some embodiments, the wireless communication portion also includes an optical sensor 26, a microcontroller unit 20, a memory, a power regulator, and a power source (e.g., a battery).

In some embodiments, the sensing portion includes a humidity sensor. As previously described, a membrane filter 48 is placed over the sensor. In some embodiments, the sensing portion includes one or more sensing components that sense a plurality of properties. In some embodiments, the sensing portion includes one or more sensing components that sense relative humidity and temperature.

The separate sensing portion is connected to the wireless communication portion via an electrical cable 106, and enables the placement of the sensing portion deep (e.g., more than about 2 feet, more than about 6 feet, or more than about 8 feet from the nearest surface of the building material structure) within a building material structure (e.g., a thick concrete slab) while the wireless communication portion is placed closer to the surface of the building material structure (e.g., less than about 1 foot, less than about 8 inches, or less than about 6 inches from the nearest surface of the building material structure). Such a configuration enables effective transmission of a wireless communication signal out of the building material structure (e.g., a thick concrete slab), while sensing properties from portions deep within the center region of the building material structure.

The electrical cable may include a power line, a data line, a clock line, and/or a ground line that are electrically connected to the sensing component(s) in the sensing body, which provides power and signals to operate the sensing component(s) and to send sensed data from the sensing portion to the wireless communication portion. In some embodiments, the electrical cable has a length greater than about 2 feet (e.g., about 3 feet). In some embodiments, the electrical cable has a length greater than about 6 feet (e.g., about 8 feet).

In some embodiments, at least one of the wireless communication portion and the sensing portion includes an overmolded body, as may be formed using methods similar to that described for FIG. 4. In some embodiments, the wireless communication portion includes an overmolded body. In some embodiments, the sensing portion includes an overmolded body. In some embodiments, the wireless communication portion and the sensing portion include overmolded bodies.

Figure 10A:
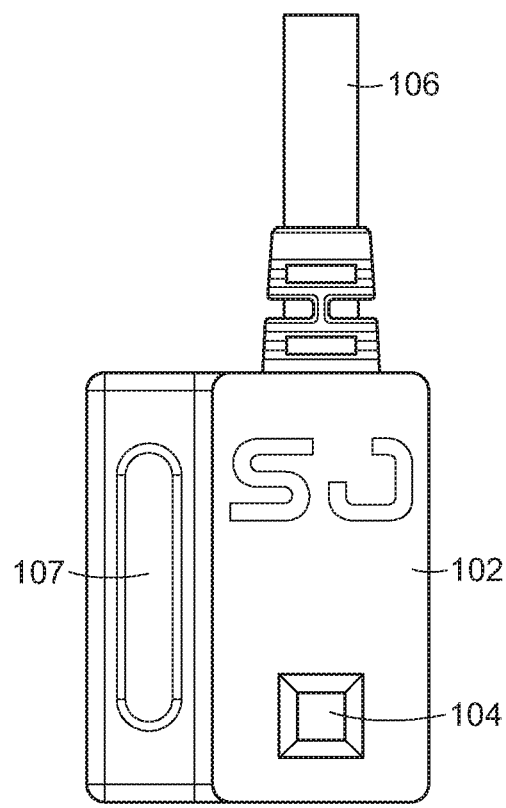
FIGS. 10A and 10B are top and side views, respectively, of the sensing portion of the sensor device of FIG. 9 in accordance with one or more embodiments.
Figure 10B:
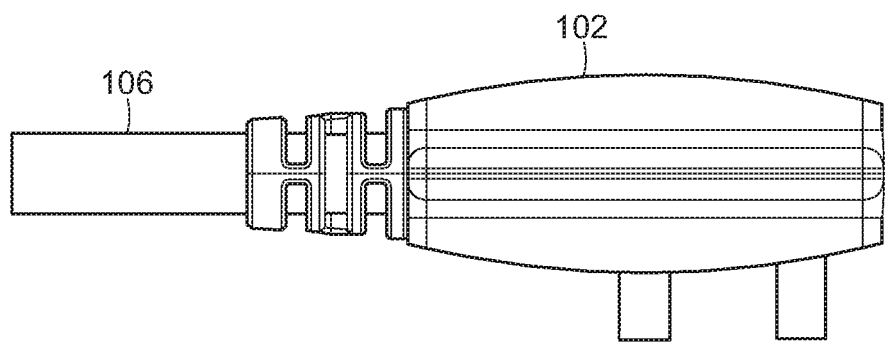

FIGS. 10A and 10B are top and side view illustrations, respectively, of the sensing portion, according to some embodiments. The sensing portion includes a sensor opening 104, which may be formed in a manner similar to the sensor opening described in FIGS. 6-8, and may include a membrane filter 48 and/or a filter supporting structure. The sensing portion includes an attachment opening 107 that enables the attachment of the sensor device 100 to construction structures using any suitable attachment methods, such as metal wires, cable ties, and/or the like.

Figure 11:
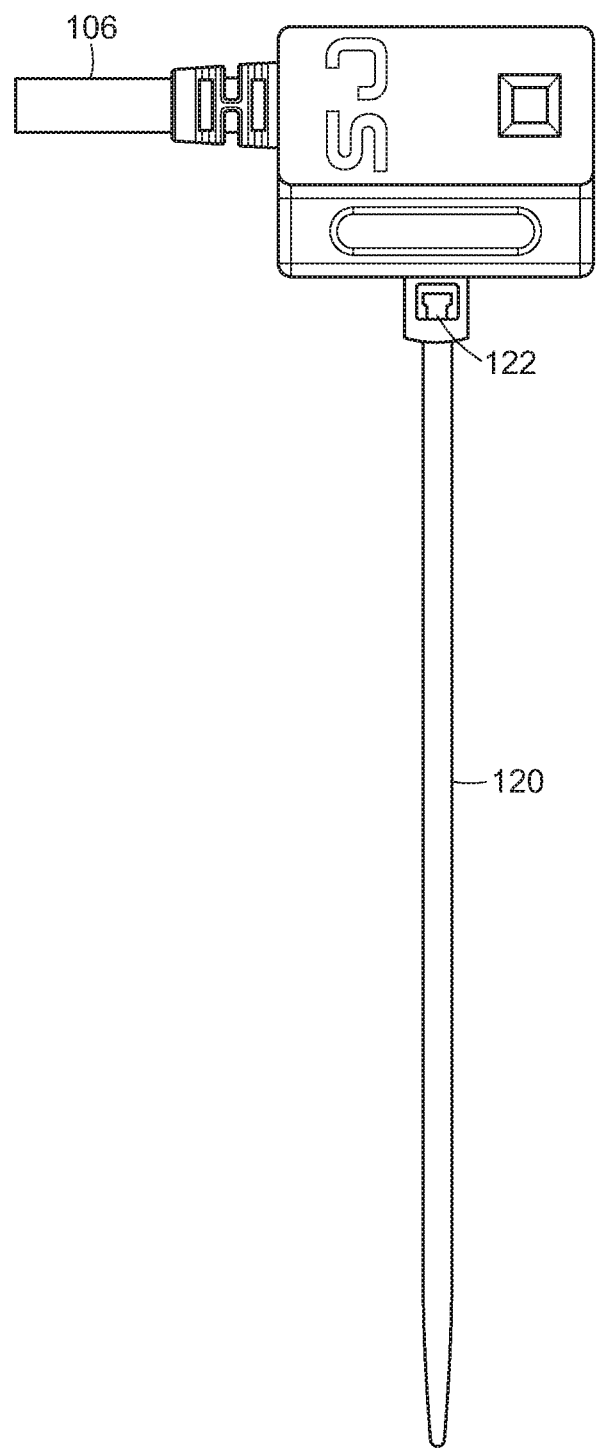
FIGS. 11 and 12 are top views of sensing portions including a cable tie and cable tie opening in accordance with one or more embodiments.
Figure 12:
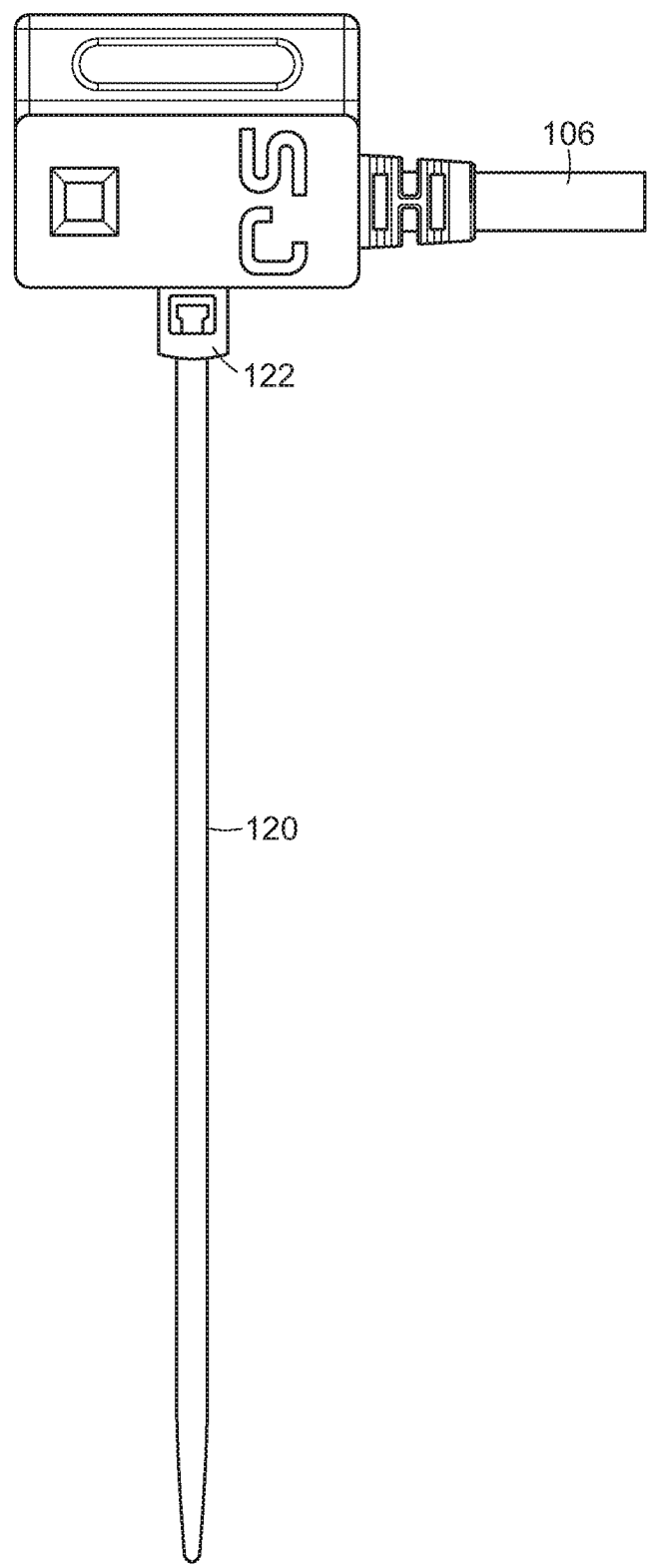

FIGS. 11 and 12 are top view illustrations of sensing portions including a cable tie 120 and cable tie opening 122, according to some embodiments. In some embodiments, the cable tie is substantially perpendicular to the electrical cable, as illustrated in these drawings.

Figure 13:
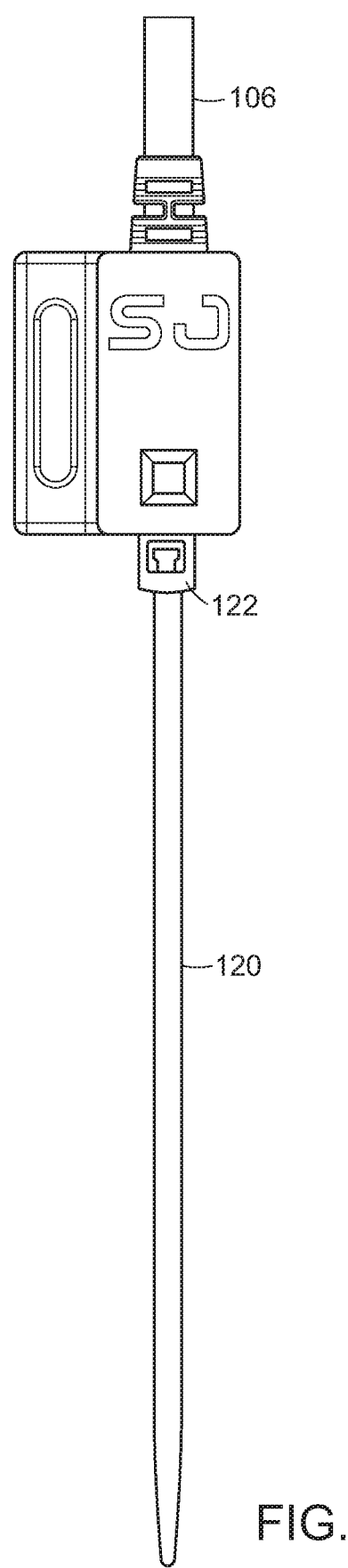
FIG. 13 is a top view of a sensing portion, in which the cable tie is substantially parallel to the electrical cable in accordance with one or more embodiments.

FIG. 13 is a top view illustration of a sensing portion including a cable tie and cable tie opening, according to some embodiments. In some embodiments, the cable tie is substantially parallel to the electrical cable, as illustrated in the drawings.

Figure 14:
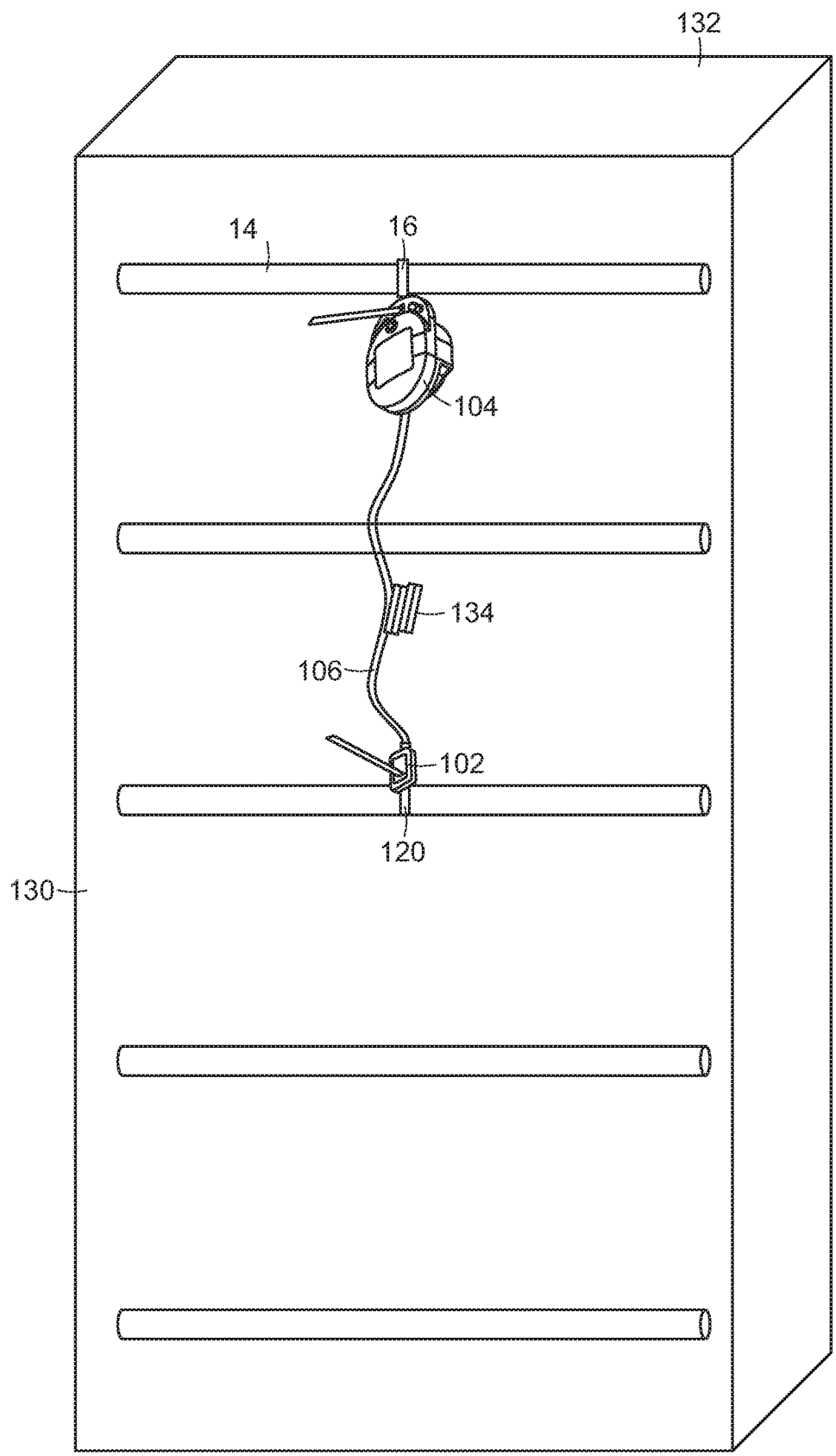
FIG. 14 is a perspective view of a sensor device including a wireless communication portion and a sensing portion embedded in a building structure in accordance with one or more embodiments.

FIG. 14 is a perspective illustration of a sensor device including a wireless communication portion and a sensing portion in use within a building structure 130 (e.g., a concrete slab with rebar frame), according to some embodiments. As illustrated, and previously described, the sensing portion may be attached to rebar 14 deep within the concrete slab, whereas the wireless communication portion may be attached to rebar 14 closer to a surface 132 of the concrete slab, thereby enabling effective wireless communication with an external device (e.g., a smartphone 18).

Figure 15:
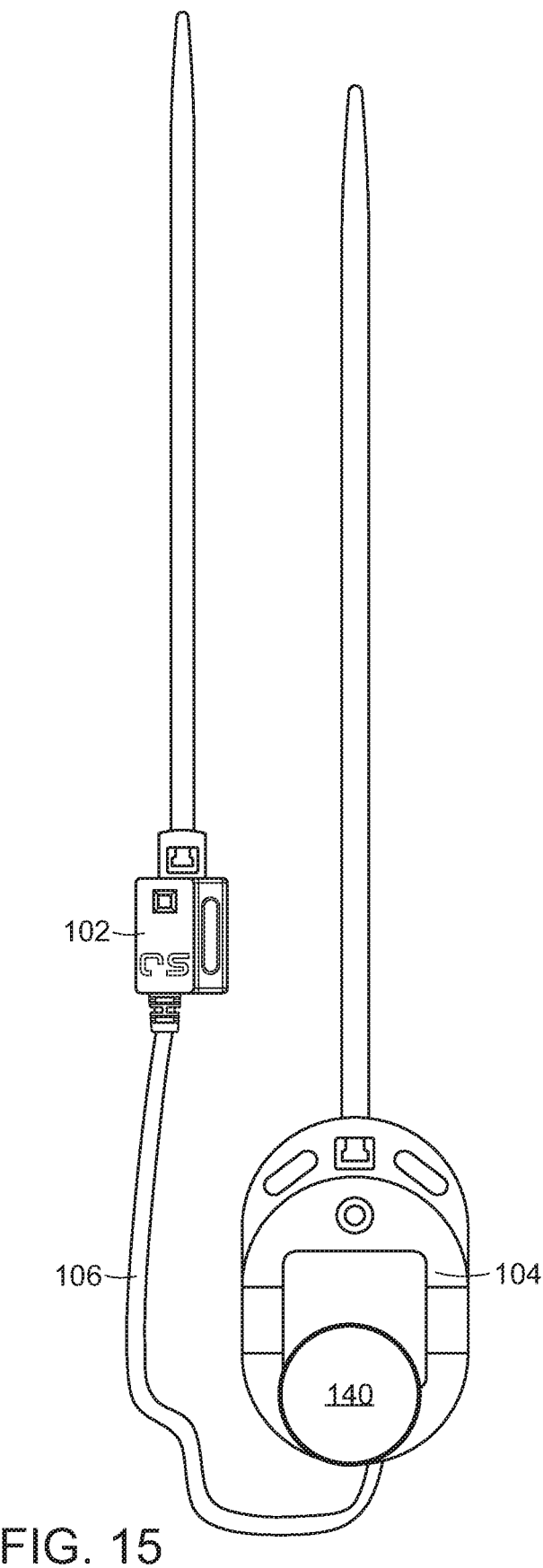
FIG. 15 is a top view illustrating a sensor device including a retractable electrical cable mechanism in accordance with one or more embodiments.

FIG. 15 is a top view illustration of a sensor device including a retractable electrical cable mechanism 140, according to some embodiments. In some embodiments, the retractable electrical cable mechanism includes a spring loaded assembly (or any other suitable retraction mechanism) that retracts the electrical cable. Using such a mechanism, a long electrical cable (e.g., greater than about 6 feet) may be easily manipulated without the need for an installer to handle spare portions of the electrical cable. Furthermore, when only a shorter portion of electrical cable is needed, the installer need not bother securing spare portions of the electrical cable as shown in FIG. 14 at 134.

Figure 16:
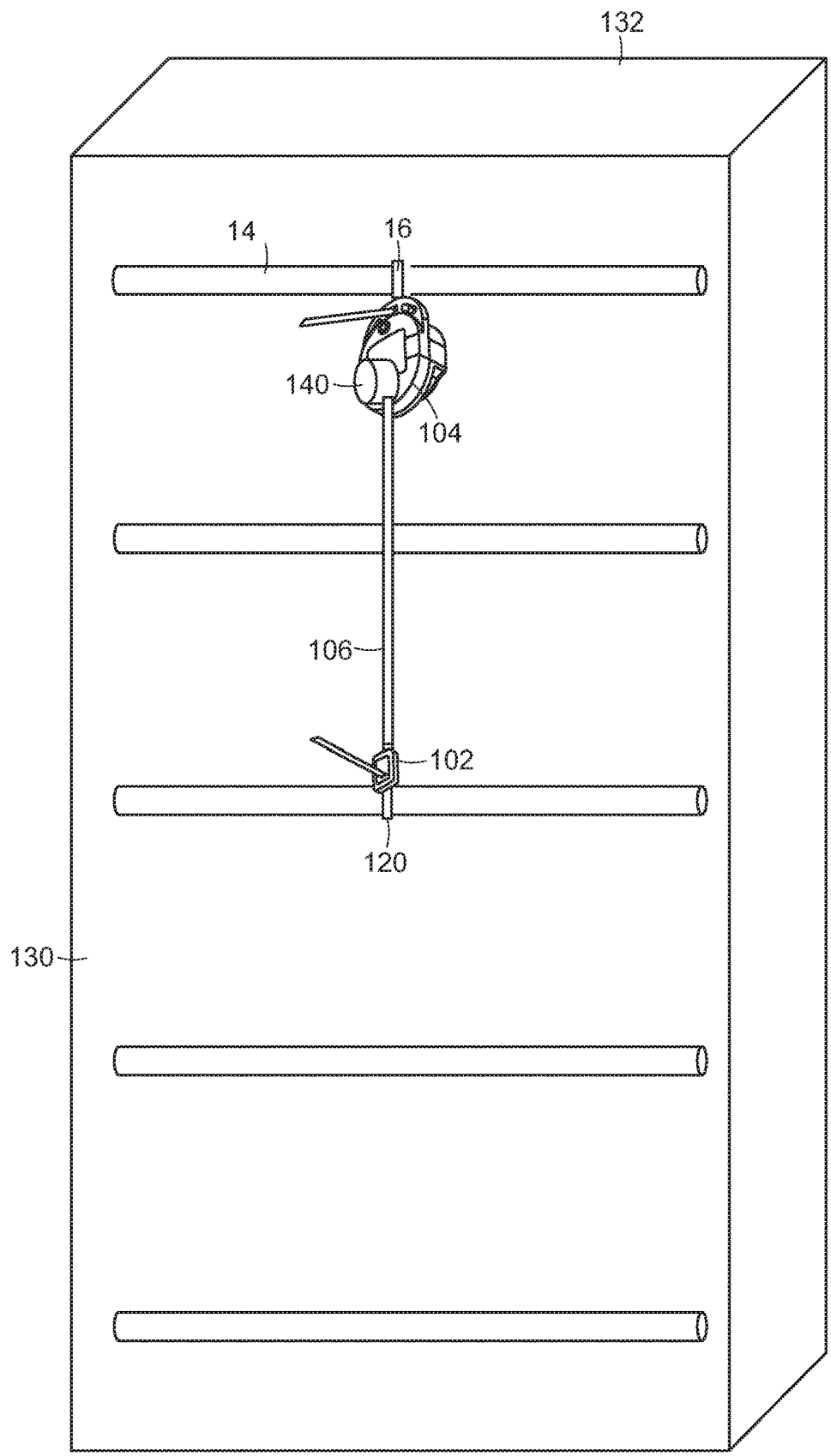
FIG. 16 is a perspective view of the sensor device of FIG. 15 embedded in a building structure in accordance with one or more embodiments.

FIG. 16 is a perspective illustration of a sensor device including a wireless communication portion, a sensing portion, and a retractable electrical cable mechanism in use within a building structure (e.g., a concrete slab with rebar frame), according to some embodiments.

In accordance with one or more embodiments, each sensor device includes multiple sensing portions 102, each being connected to a single wireless communication portion 104 by a separate electrical cable. Each sensing portion can be embedded at a different location in the building structure.

In accordance with one or more embodiments, each sensor device 10 includes a power amplifier system to improve communication with smartphones. The power amplifier system can include a power and low-noise-amplifier "frontend" system to both boost the output power while also boosting the receiver gain so the device is more sensitive to incoming signals to the device.

In accordance with one or more embodiments, the sensor device 10 also includes a power saving feature to reduce power usage by the amplifier system and thereby increase battery life. In accordance with one or more embodiments, the sensor device 10 uses certain heuristics to determine when to turn on the power amplifier system. For instance, the sensor device can broadcast some of the time using the power amplifier and some of the time without it. The device records whether incoming connections from a smartphone occurred with the amplifier on or off. If connections occur with the amplifier off, use of the amplifier is discontinued. Otherwise, the amplifier is used for subsequent communications.

In accordance with one or more further embodiments, the power amplifier enables an M2M network, where a sensor device can be connected to either another sensor device (e.g., in a mesh network) or to a relay to subsequently transmit the data up to the cloud. In this implementation, the smartphone retrieves sensor data from the cloud.

In accordance with one or more further embodiments, the power amplifier enables an M2M network, where a sensor device can be connected to another sensor device (e.g., in a mesh network), and the sensor devices cooperate to wirelessly communicate sensor directly to a smartphone.

Sensor Firmware

The following describes the general functionality of an exemplary sensor in accordance with one or more embodiments and its interaction with a smartphone app (also referred to herein as the "client").

Assembly Process

When the sensors are first assembled, a simple quality control program is programmed onto the PCBs that runs various diagnostic procedures to ensure the sensor is assembled properly. If this program detects a failure, it flashes an LED in a specific pattern to indicate to the technician what failure was detected. If, however, no problems are detected, the LED is held in a steady state for 2 seconds before shutting off and going into lowpower "off" mode. Because the battery for the sensor is permanently attached to the sensor at this point, the quality control program should be conservative with power usage.

As part of the QC program procedure, the non-volatile memory in the sensor is initialized with default state information that is later used by the sensor firmware. The state is written as "ASSEMBLY".

Later, when the sensor firmware has been programmed onto the sensor, it detects if the non-volatile memory state has been initialized and is in ASSEMBLY mode. If so, the sensor shuts down for period of time so a technician can complete the packaging process. After this interval, the sensor starts up and assumes it is inside a package.

When the sensor is inside a package, it retrieves an optical sensor reading every few seconds. If two consecutive readings indicate the sensor is in light, it transitions to the "waiting for pour" state.

When the sensor is installed while waiting for a pour, it sends a BLE advertisement about every 2 seconds. The sensor collects a temperature reading every 30 minutes for the first 60 days and RH reading every 24 hours. The sensor retrieves an optical sensor reading every 5 minutes. If consecutive readings over 18 hours indicate the sensor is in darkness, it transitions to the "encased" state. Otherwise, the sensor resets collected sample data, increment the light resets counter by 1, and continues monitoring optical data.

When the sensor is embedded within concrete, it sends a BLE advertisement about every 2 seconds. It collects a temperature reading every 30 minutes for the first 60 days and RH reading every 24 hours. The sensor checks for the presence of light every 15 minutes. If light is detected once, the sensor clears existing data, and transitions back to the "waiting for pour" state. If no light is detected for 30 consecutive days, the sensor stops checking for light.

Advertised Bluetooth Services

The Bluetooth advertisement uses a special format for the broadcast name of the device: 05-S[12 characters], e.g., 05-Sabcdefghijkl.

This naming format includes the sensor firmware version ("05") as well as a delimiter ("S"). The remaining 12 characters are a unique identifier for the sensor based on the MAC address.

Following this format indicates to the smartphone app that: (a) it is likely a Concrete Sensor due to the unique nature of the string format, (b) the version of the protocol to use when communicating with the sensor, and (c) a way of uniquely identifying the sensor from any others.

Further, there is a QR code affixed to the front of each sensor. This QR code encodes the unique 12 character address of the device. This allows the smartphone app to correlate an image of the sensor with a BLE advertisement.

Device Information

A characteristic to print basic information about the sensor, such as the protocol version.

Data Service

This service is comprised of 7 individual characteristics:
1. A readable characteristic reporting the total number of temperature samples recorded by the sensor.
2. A writable characteristic, called a "cursor", indicating how many samples the smartphone has previously retrieved.
3. A readable characteristic that transmits all temperature samples starting with the "cursor" (or 0)
4-7 are identical to 1-3 but for RH values instead of temperature.
7. A readable characteristic indicating the number of light-based resets (explained below).

System Service

A characteristic to read the number of watchdog resets that have occurred

A characteristic to force the device to change state

To use this characteristic, a special, secret code is written to force the sensor to change state, or to clear all data and reset. This code is kept secret and only intended to be used as part of an onsite diagnostic by a technician.

Process of Connecting a Client to the Sensor Over Bluetooth
1. When the client connects, it first reads basic state and diagnostic information about the sensor, including the light resets count and the watchdog resets count.
a. If the light resets count has increased from a previously read value (starting at 0), the client deletes all previously retrieved samples.
2. The client next reads the total number of temperature samples, then the total number of RH samples. These values are used on the client side to (a) indicate to the user the progress of data retrieval, and (b) when to stop polling the sensor for sample data.
3. The client checks how many previously retrieved temperature and RH samples it has. It then writes these two numbers to the corresponding characteristics on the device. For instance, if the client had previously retrieved 25 temperature samples, it writes "25" to the temperature cursor characteristic.
4. The client then polls the sensor for temperature and RH readings. The sensor starts sending back readings at the cursor+1 and continues for each successive request until all samples have been transmitted.
5. The client disconnects Process of Retrieving Optical Sensor Readings
1. Retrieve 3 samples from the phototransistor
2. Determine variance of each sample using algorithm such as disclosed in http://en.wikipedia.org/wiki/Algorithms_for_calculating_variance#Online_algorithm
3. Remove the sample with the greatest variance
4. Average the two remaining values
5. Check if the result is greater or less than the preset darkness threshold
6. Write to the EEPROM a counter indicating how many consecutive readings of light or dark the sensor has detected.

Process of Collecting Temperature and RH Readings
1. Turn on power to the sensing chip
2. Retrieve 3 samples from the sensing chip of either temperature or RH
3. Turn off power to the sensing chip
4. Convert the raw reading from the sensing chip to a value of either Celsius or a percentage, using the formulae provided by the sensing chip manufacturer
5. Determine variance of each sample using algorithm such as disclosed in httplien.wikipedia.orewiki/Algorithms_for_calculating_variance#Online_algorithm
6. Remove the sample with the greatest variance
7. Average the two remaining values
8. Store the result onto the long term storage system (EEPROM)

Process of Storing Samples

A long term, nonvolatile memory system is available for sample storage (an EEPROM)

The EEPROM is divided up into three logical sections:
1. Temperature samples (first 5760 bytes)
2. RH samples (remaining space on the EEPROM)
3. Sensor state information (last 14 bytes)

The temperature and RH data are stored as 2 byte hexadecimal integers. The sensing chips report a floating point value of either temperature in Celsius or a percentage (RH). This floating point number is multiplied by 100, rounded off to the nearest integer, and stored. Later, when the client has retrieved these values, it divides by 100 to find the correct 2 decimal place value. These values are stored as two's complement, allowing for negative values (for instance, subzero temperature readings).

Smartphone and Sensor Communications Overview

The following describes how the smartphone app communicates with the sensor in accordance with one or more embodiments.

Adding a New Sensor to the Smartphone App

Figure 17:
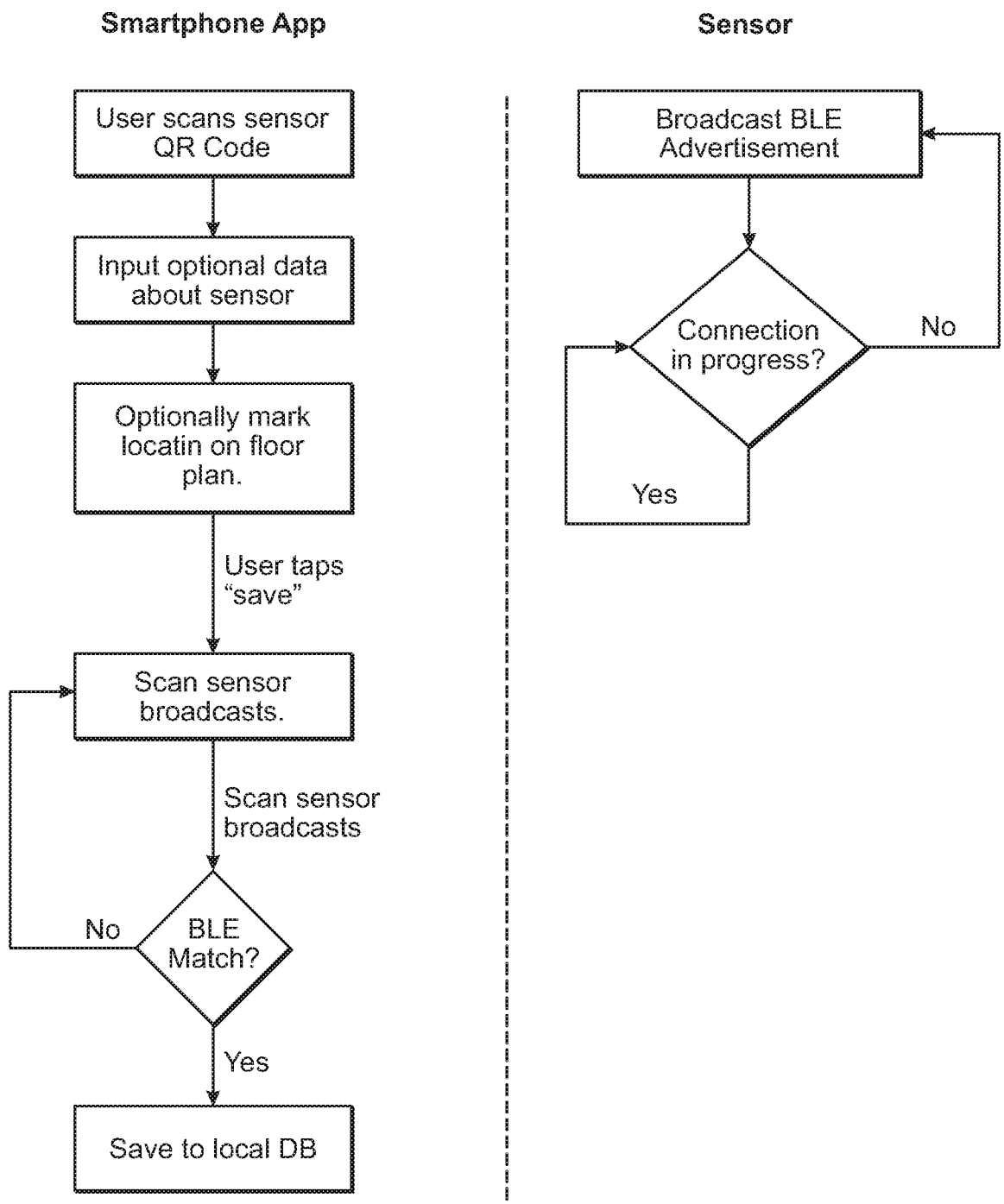
FIG. 17 is a flowchart illustrating an exemplary process for adding a sensor device to a set of sensor devices used at a given site or area in accordance with one or more embodiments.

The smartphone app performs a number of functions, one of which is to organize and communicate with individual sensors. As shown in FIG. 17, there are two ways to add a sensor: (1) A sensor can be added by scanning the QR code affixed to the front of the plastic sensor housing; and (2) A sensor can be added by searching for nearby peripherals.

In the first scenario, a user has removed a new sensor from its packaging and now wants to add this sensor to the smartphone app. The sensor turns on automatically when removed from its packaging and begins broadcasting a Bluetooth Low Energy advertisement packet (see above). The smartphone app turns on the built-in camera feature, which the user points at the QR code to scan.

The QR code is a representation of the sensor's MAC address, which indicates to the smartphone app what BLE advertisement to look for. If it finds a match, the sensor is added to the smartphone app database (and sync'd). If it doesn't find a match after a period of time, it alerts the user who is unable to proceed with adding the sensor.

The sensor is periodically broadcasting BLE advertisements except while there is an in-progress BLE connection (described in further detail below).

BLE Advertisement

Each sensor periodically broadcasts a Bluetooth advertisement packet. These packets are broadcast at approximately 2 second intervals.

Figure 18:
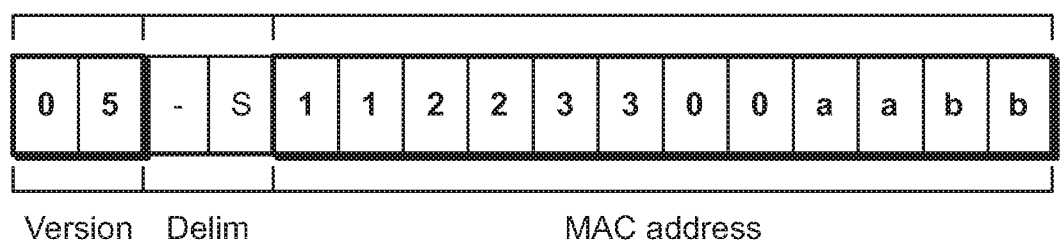
FIG. 18 illustrates an exemplary format for a Bluetooth advertisement packet periodically broadcast by a sensor device in accordance with one or more embodiments.

The packets are constructed using a format illustrated in FIG. 18.

Version: indicates the sensor firmware running on this particular sensor. It allows the system to make modifications to the protocol the sensor and smartphone app will use to communicate and eliminates the need to negotiate with a round-trip Bluetooth message when first connecting.

Delim: This is a separator from the version number and MAC address. It also makes it more clear which advertising peripheral is a Concrete Sensors sensor and not some other device, reducing the likelihood of attempting to connect to some other Bluetooth peripheral that happens to be broadcasting a similarly formatted packet.

MAC address: Unique identifier, used to separate one sensor from another. Factory-determined unique number.

Retrieving Data from a Sensor

Figure 19:
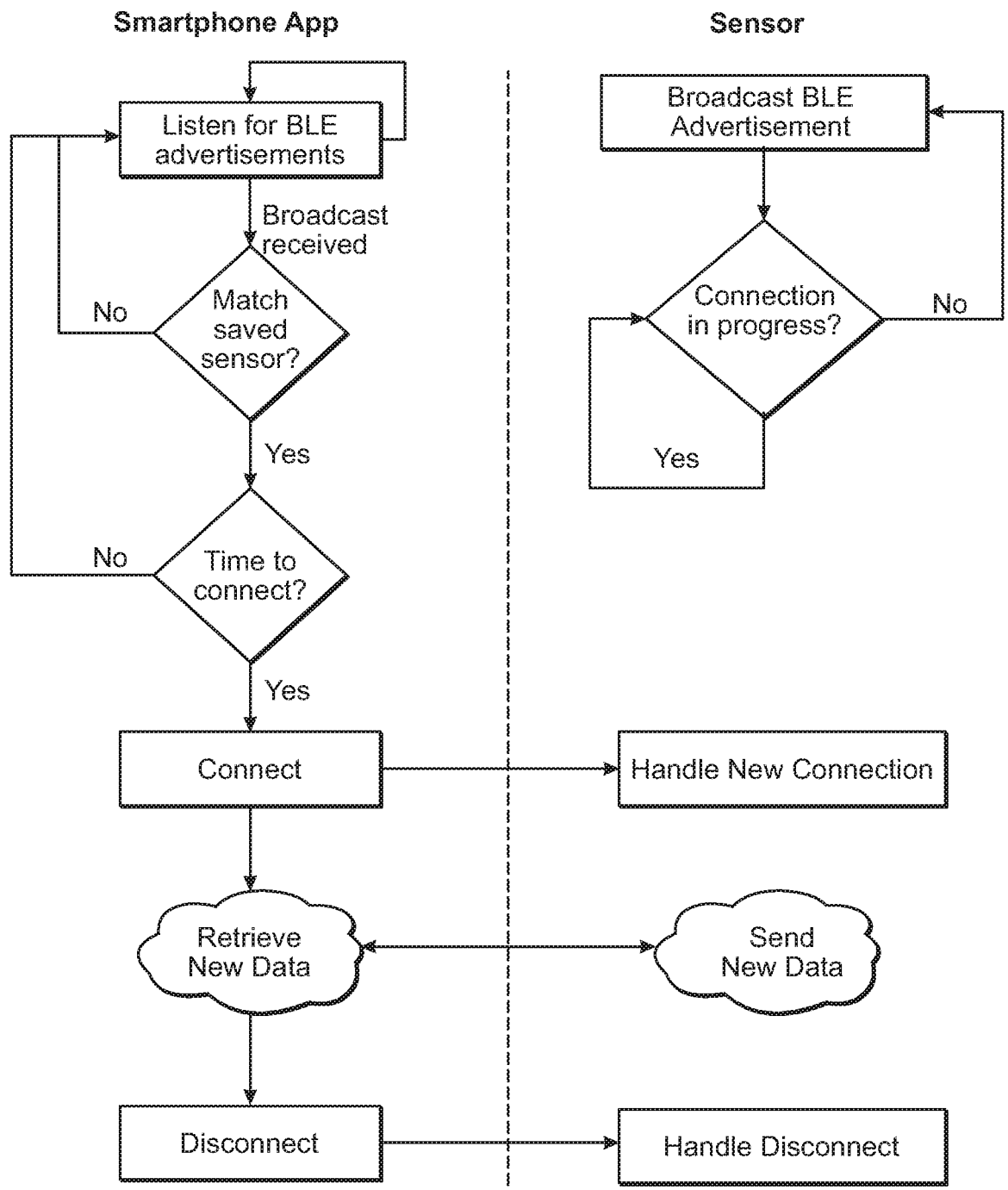
FIG. 19 is a flow diagram illustrating an exemplary process for retrieving data by a smartphone app from a sensor device in accordance with one or more embodiments.

As shown in FIG. 19, once a sensor has been added, the smartphone app will attempt to periodically connect to it to retrieve updated data.

Whenever the app is running, it is listening for BLE advertisements that match the expected broadcast pattern detailed above in BLE Advertisement. When one of these advertisements is found, the app will check:
1. that the MAC address matches a previously added sensor in its database, and
2. the smartphone app hasn't already connected to the sensor in the last 30 minutes (this prevents reconnecting to a sensor when there is no new data to retrieve).

Additionally, the smartphone app will not connect to a sensor if it is already engaged in synchronizing other data to/from the cloud (to prevent potential collisions with other data).

While a connection is in progress, the sensor stops sending BLE advertisements. This is a limitation of the Bluetooth implementation and may change in the future.

Figure 20:
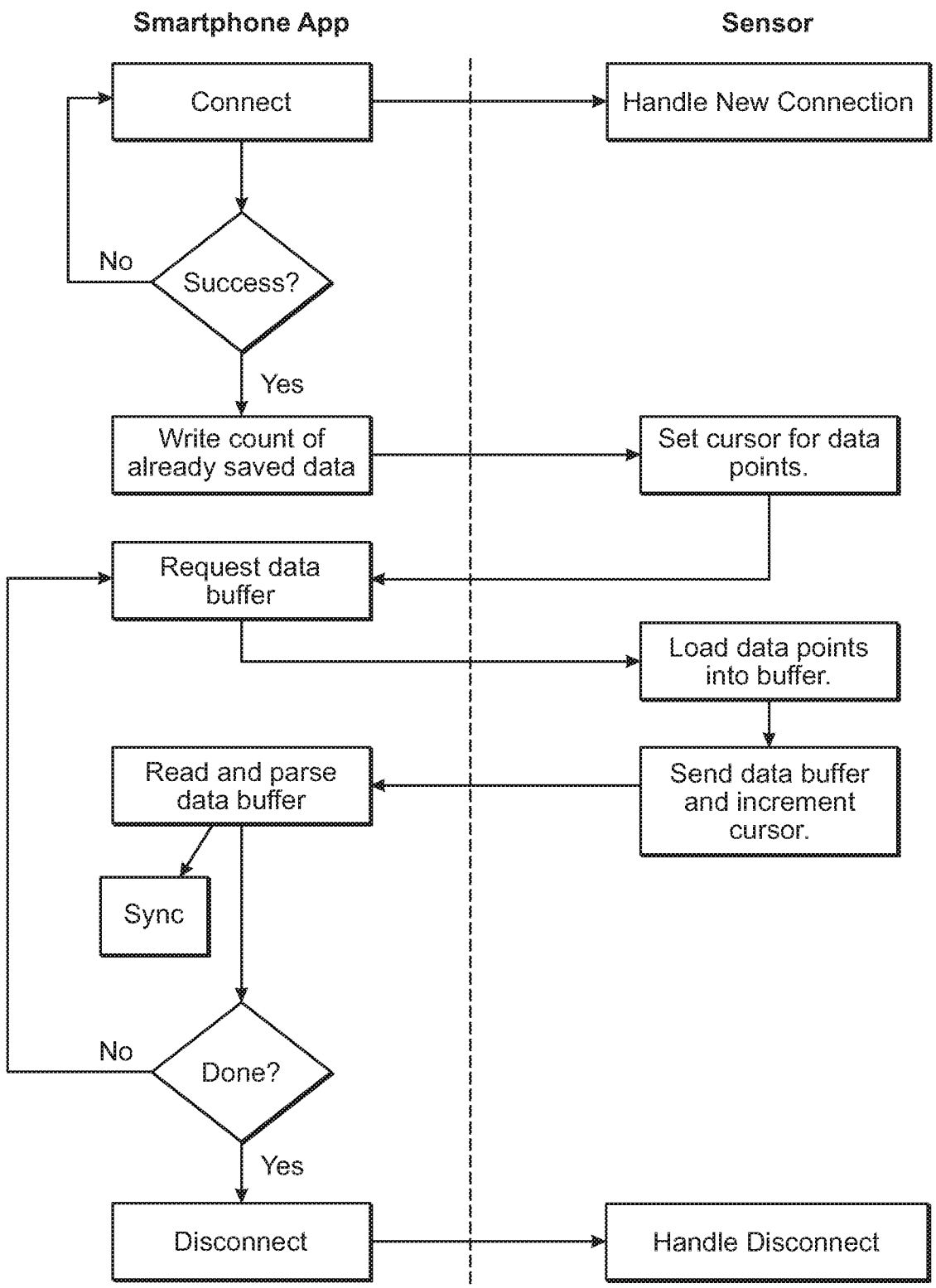
FIG. 20 is a flow diagram illustrating further details of the process for retrieving data by a smartphone app from a sensor device in accordance with one or more embodiments.

FIG. 20 provides additional detail of how the data retrieval process works (the highlighted section in FIG. 19):

Because the sensor has a limited battery life, it is important to minimize the number of packets sent back and forth and the time it takes to complete a retrieval. To this end, the smartphone app attempts to only retrieve the data it does not already have. Further, all data is progressing forward in time: once data has been retrieved, it will never be changed and thus should not be re-downloaded.

Two distinct sets of data are collected: temperature and relative humidity. Both data sets are handled in an identical way, but retrieved in separate operations. This means that the smartphone app connects and follows the FIG. 20 process first for temperature data, then repeats the same steps for relative humidity. The process is as follows:
1. After connecting to the sensor, the smartphone app first retrieves the sensor's current light resets count number. See Handling Light Resets section below for more information.
2. Next, the smartphone app retrieves the total count of temperature samples and the total count of RH samples. These numbers are used to show a progress bar to the user and to calculate the likely date and time of a sample.
3. Next, the smartphone app determines what data it has previously retrieved (either by directly connecting to the sensor, or by synchronizing with the cloud from someone else who has directly connected to the sensor). This count is written to the sensor as the "cursor" and indicates the starting point that new data should be retrieved from. The temperature count is the first one written.
4. Finally, the smartphone app continuously requests a new packet of data until it determines there is no more data to retrieve. It then either repeats the process for RH data, or disconnects.

Data Packets

Figure 21:
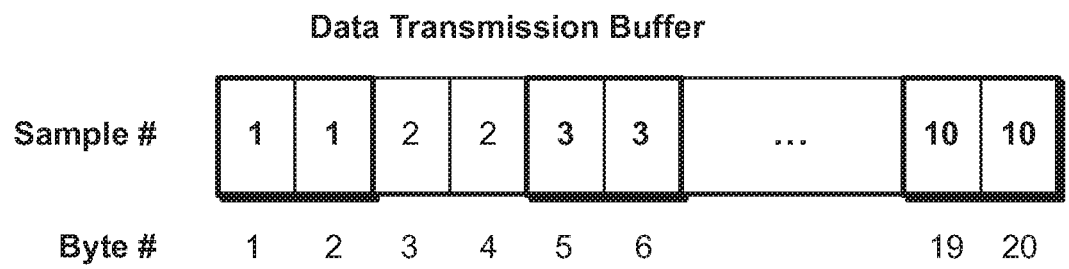
FIG. 21 illustrates an exemplary data packet received at the smartphone app from a sensor device in accordance with one or more embodiments.

An exemplary data packet is illustrated in FIG. 21. Each packet has 20 bytes in total, made up of two-byte samples in hexadecimal. Each two-byte sample is divided by 100 to find the decimal equivalent. Two examples:
Temperature: 0x9A9→2473→24.73° C.
Relative Humidity: 0x1D1B→7451→74.51%

Figure 22:
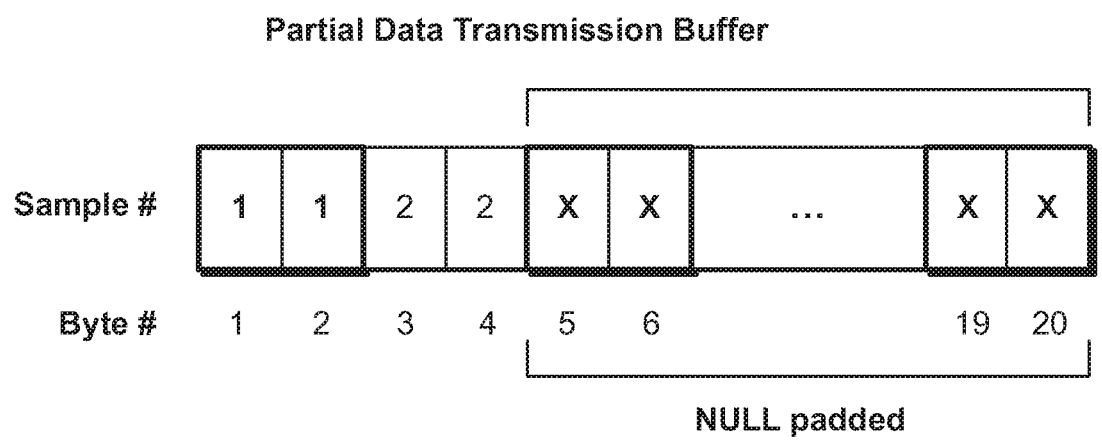
FIG. 22 illustrates an exemplary data packet received at the smartphone app from a sensor device in accordance with one or more embodiments.

To determine when data is complete, the sensor pads a buffer with NULL (or returns a buffer with only NULL). For instance, when the smartphone app finds a NULL (FIG. 22), it knows there is no more data to retrieve and stops requesting more (if it was temperature, it then moves on to requesting relative humidity data; otherwise it disconnects).

Parsing Data

Figure 23:
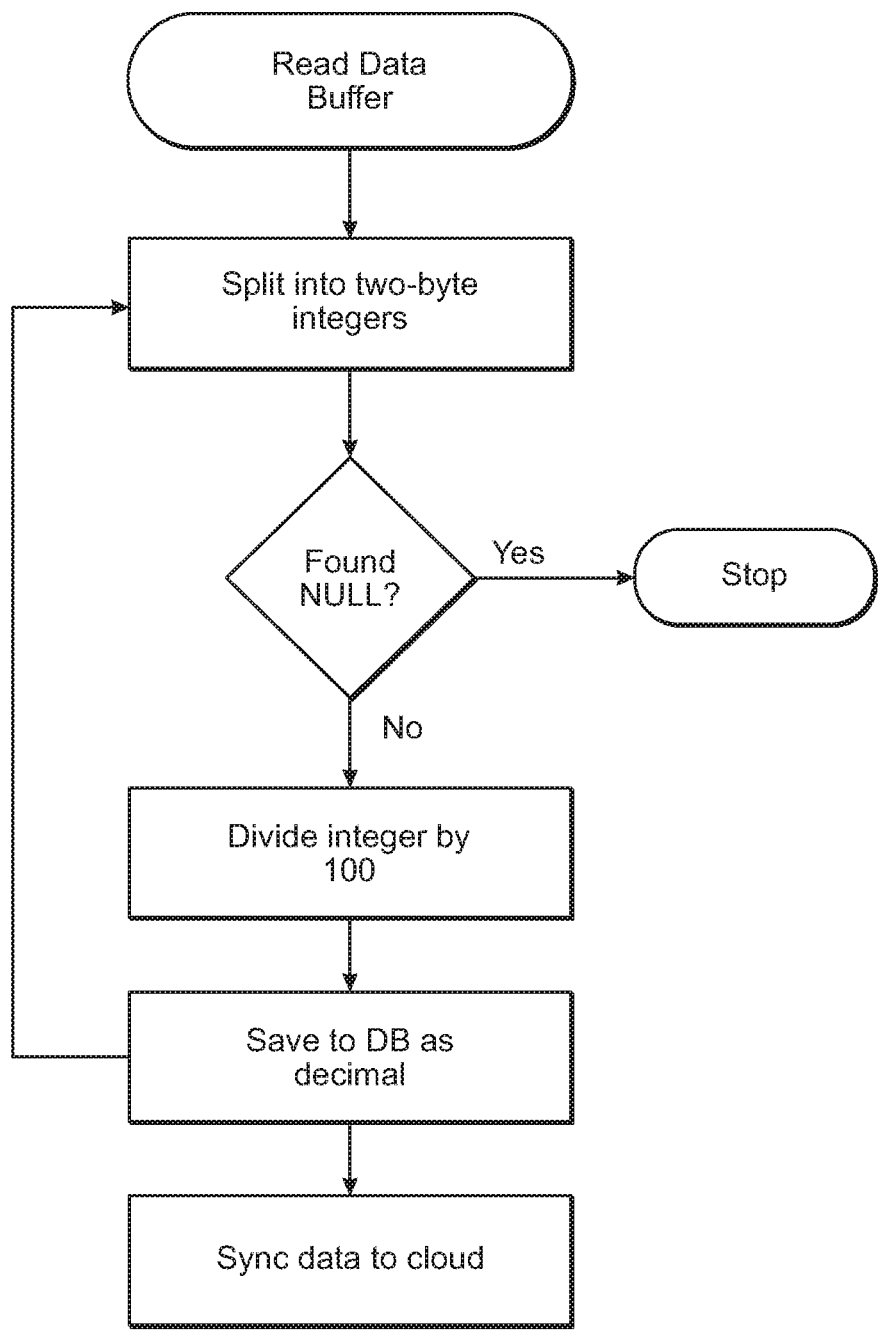
FIG. 23 is a flow chart illustrating an exemplary parsing process by the smartphone app of data received from a sensor device in accordance with one or more embodiments.

As shown in FIG. 23, as data is retrieved from the sensor, the smartphone app begins parsing it. The parsing process takes the data packet, splits it up into individual two-byte samples and performs the conversion process detailed above to find the decimal equivalent. In addition, the smartphone app also determines the date the sample was taken (detailed below).

While the smartphone app is retrieving data, it is possible for a connection to be severed and data retrieval to end prematurely. If this happens, the smartphone app parses and stores the data is had retrieved and attempts to establish a new connection (where it will then write a new cursor to pick up where it left off).

Determining Sample Date and Time

In one or more embodiments, the sensor does not have an onboard clock and has no concept of when a sample was taken. It can only determine relative times (e.g., 30 minutes from a previous event). As a result, the smartphone app determines the likely time of when a particular sample was taken. The accuracy of this is +/−30 minutes during the first 60 days of the sensor operation, and +/−24 hours thereafter, explained below:

If the smartphone app has never connected to a sensor before, and the sensor is still recording temperature data (which occurs every 30 minutes during the first 60 days), the smartphone app:
1. Retrieves the total count of all temperature and RH data
2. Takes the current date and time
3. Subtracts (30 minutes*number of temperature samples taken) from the current date and time, and sets this result as the time of the first temperature and RH samples.
4. Future temperature and RH samples are then determined using this basis.

In a similar vein, if the smartphone app has never connected to a sensor before, and the sensor has completed recording temperature data (but still recording RH data), the smartphone app:
1. Retrieves the total count of all temperature and RH data
2. Takes the current date and time
3. Subtracts (24 hours*number of RH samples taken) from the current date and time, and sets this result as the time of the first temperature and RH samples.
4. Future temperature and RH samples are then determined using this basis.

This has been found to be an acceptable level of accuracy for end users. In an alternate embodiment, a clock may be added to the sensor. This be set by the smartphone app when adding the sensor for the first time.

Handling Light Resets

The sensor has no mechanical switch and instead uses an ambient phototransistor tuned to detect human-visible light wavelengths to determine interesting events. This phototransistor is constantly being polled to determine what state the sensor should be in.

When the sensor is first assembled, it is placed into an interim state (called "ASSEMBLY"). As soon as the sensor is programmed with its firmware, it transitions to the "IN_PACKAGE" state. While in this state, the sensor will periodically check for light, indicating it's been removed from its packaged and is being installed.

Figure 24:
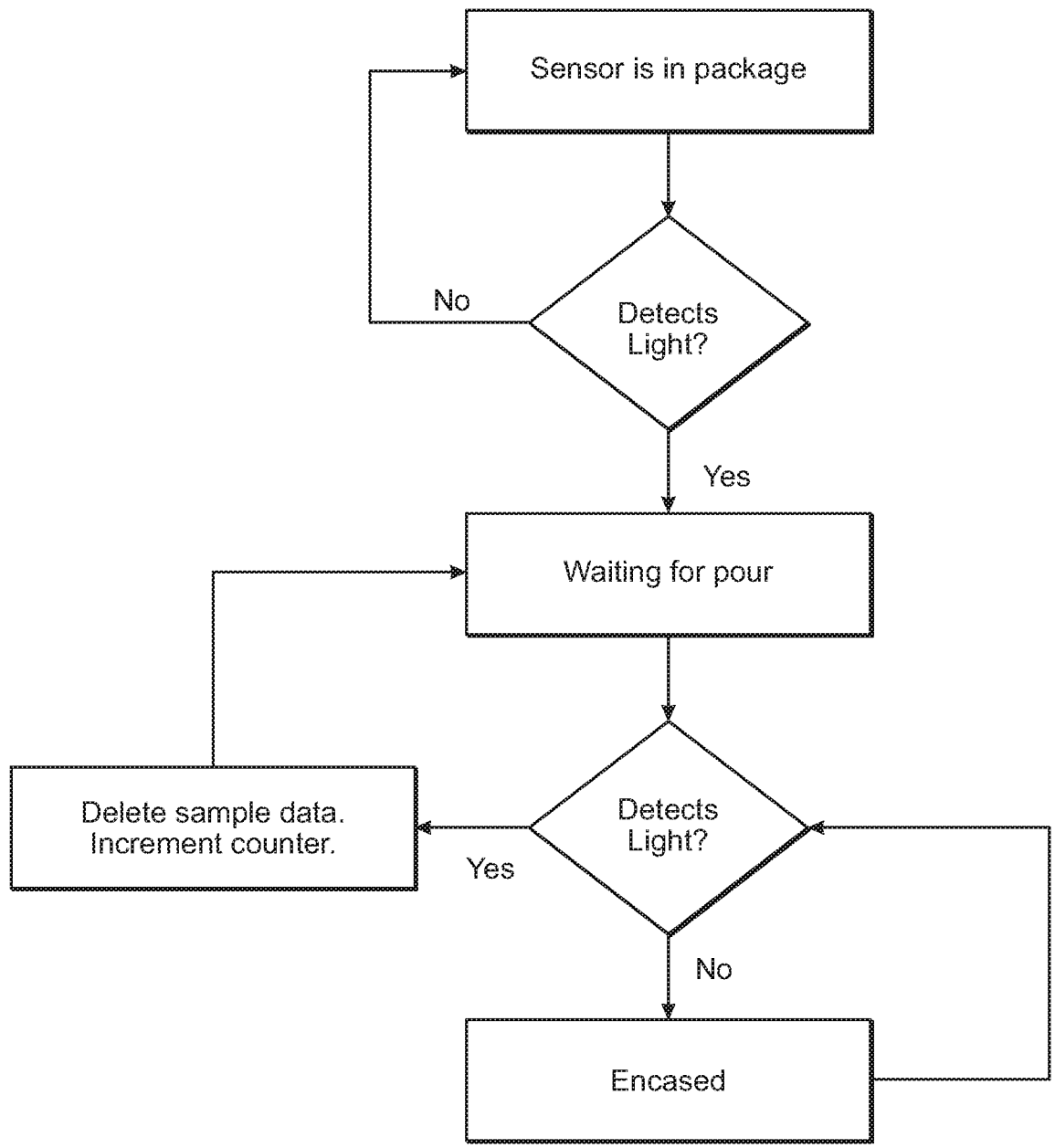
FIG. 24 is a flow chart illustrating an exemplary process of activating a sensor device in accordance with one or more embodiments.

After being taken out of the packaging, the sensor waits for concrete to be poured around the sensor, encasing it. Whenever light is detected, the sensor all of the temperature and relative humidity data it has previously recorded, increments a light resets counter, and proceeds as FIG. 24 details.

When the smartphone app connects to a sensor to retrieve data, it requests the current light resets count. If this number is greater than the light resets count for that sensor the smartphone app had previously recorded, the smartphone app deletes all of its temperature and relative humidity data and proceeds with retrieving new data from the sensor.

A sensor will never see light while it's encased in concrete, so any time light is detected in that state, the sensor must not be concrete (and thus it resets the data it had previously collected and starts over). The smartphone knows when data has been reset because of this by virtue of the light resets counter having increased.

While the exemplary embodiments disclosed herein refer to use of a smartphone in the concrete sensor system, it should be understood that various other computer devices may also be used in the system including, without limitation, personal computers, tablet computers, wearable computers (e.g., smart watches and smart glasses), personal digital assistants, and generally any computer device capable of communicating wirelessly with the sensor devices. The computer devices include operating systems (e.g., Android, Apple iOS, and Windows Phone OS, among others) on which applications run. The operating systems allow programmers to create applications or apps to provide particular functionality to the devices. A representative computer device includes at least one computer processor and a storage medium readable by the processor for storing applications and data. The computer device also includes input/output devices including a display for visual output, e.g., an LCD or LED display, which may have touch screen input capabilities.

Having thus described several illustrative embodiments, it is to be appreciated that various alterations, modifications, and improvements will readily occur to those skilled in the art. Such alterations, modifications, and improvements are intended to form a part of this disclosure, and are intended to be within the spirit and scope of this disclosure. While some examples presented herein involve specific combinations of functions or structural elements, it should be understood that those functions and elements may be combined in other ways according to the present disclosure to accomplish the same or different objectives. In particular, acts, elements, and features discussed in connection with one embodiment are not intended to be excluded from similar or other roles in other embodiments. Additionally, elements and components described herein may be further divided into additional components or joined together to form fewer components for performing the same functions. Accordingly, the foregoing description and attached drawings are by way of example only, and are not intended to be limiting.

The invention claimed is:

1. A portable computer device comprising:
at least one processor;
memory associated with the at least one processor;
a communication module connected to the at least one processor for receiving data wirelessly from a plurality of sensor devices; and
a program supported in the memory for monitoring properties of a building structure, the program having a plurality of instructions stored therein which, when executed by the at least one processor, cause the at least one processor to:
(a) receive data via the communication module from the plurality of sensor devices, said plurality of sensor devices being embedded in the building structure;
(b) calculate a plurality of metrics relating to the building structure based on the data received in (a);
(c) record locations on a floorplan where each of the plurality of sensor devices is positioned; and
(d) synchronize information relating to said sensor devices or the building structure with portable computer devices operated by other users.

2. The portable computer device of claim 1, wherein (c) is performed using a pin-drop tool.

3. The portable computer device of claim 1, further comprising a display, and wherein the program further comprises instructions for generating graphs from the metrics calculated in (b) and displaying the graphs on the display of the portable computer device or sharing the graphs with other computer devices.

4. The portable computer device of claim 1, further comprising a display, and wherein the program further comprises instructions for receiving and displaying graphs on the display from a remote computer system, said graphs being generated by the remote computer system based on data received from the plurality of sensor devices.

5. The portable computer device of claim 1, wherein the metrics includes building structure strength, seismic events, vibration effects, material pH levels, gas and particle presence, structure load, crack detection, mold formation, and moisture presence.

6. The portable computer device of claim 1, wherein the building structure comprises concrete, asphalt, or epoxy, and the one or more properties comprise building structure temperature, vibration, pH, gas and particle presence, load, acoustic properties, and relative humidity.

7. The portable computer device of claim 1, wherein the portable computer device comprises a smartphone or a personal computer.

* * * * *